US009803212B2

(12) United States Patent
Van Herpen et al.

(10) Patent No.: US 9,803,212 B2
(45) Date of Patent: *Oct. 31, 2017

(54) REGULATION OF TRANSLATION OF HETEROLOGOUSLY EXPRESSED GENES

(71) Applicant: R1 B3 Holding B.V., Ca Leiden (NL)

(72) Inventors: Marinus Maria Antonius Van Herpen, Nijmegen (NL); Jozef Maurinus Raymond Hulzink, Oosterhout (NL); Anton Felix Croes, Eindhoven (NL)

(73) Assignee: R1 B3 Holding B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/072,474

(22) Filed: Nov. 5, 2013

(65) Prior Publication Data

US 2014/0127747 A1 May 8, 2014

Related U.S. Application Data

(63) Continuation of application No. 12/781,448, filed on May 17, 2010, now abandoned, and a continuation of application No. 10/491,749, filed as application No. PCT/NL02/00638 on Oct. 4, 2002, now Pat. No. 7,829,689.

(60) Provisional application No. 60/327,003, filed on Oct. 5, 2001.

(30) Foreign Application Priority Data

Oct. 5, 2001 (EP) ..................... 01203772
Apr. 19, 2002 (EP) ..................... 02076593

(51) Int. Cl.
 *C12N 15/82* (2006.01)
(52) U.S. Cl.
 CPC ..... *C12N 15/8261* (2013.01); *C12N 15/8216* (2013.01); *C12N 15/8231* (2013.01); *C12N 15/8234* (2013.01); *C12N 15/8257* (2013.01)
(58) Field of Classification Search
 CPC .................................. C12N 15/8216
 USPC ...................................... 435/69.1
 See application file for complete search history.

(56) References Cited

U.S. PATENT DOCUMENTS 7,829,689 B2 * 11/2010 Van Herpen et al. ....... 536/24.1

OTHER PUBLICATIONS

Bate et al., Maturation-Specific Translational Enhancement Mediated by the 5'-UTR of a Late Pollen Transcript, Plant Journal, vol. 10 No. 4, pp. 613-623, 1996.

Twell et al., Isolation and Expression of an Anther-Specific Gene from Tomato, Molecular and General Genetics MGG, vol. 217, Issue 2-3, pp. 240-245 (EMBL Database, Abstract, Accession No. X15855), Jun. 1989.
Honys et al., The Translationally Repressed Pollen-Specific ntp303 mRNA is Stored in Non-Polysomal mRNPs During Pollen Maturation, Sexual Plant Reproduction, vol. 13, No. 3, pp. 135-144, 2000.
Wittink et al., The Pollen-Specific Gene Ntp303 Encodes a 69-kDa Glycoprotein Associated with the Vegetative Membranes and the Cell Wall, Sexual Plant Reproduction, vol. 12, No. 5, pp. 276-284, 2000.
Wang et al., Role of mRNA Secondary Structure in Translation Repression of the Maize Transcriptional Activator Lc1, 2, Plant Physiology, vol. 125, No. 3, pp. 1380-1387, Mar. 2001.
Kozak, Initiation of Translation in Prokaryotes and Eukaryotes, Gene, Elsevier Biomedical Press, vol. 234, No. 2, pp. 187-208, Jul. 8, 1999.
Delbecq et al., Functional Analysis of the Leader Peptide of the Yeast Gene CPA1 and Heterologous Regulation by Other Fungal Peptides, Current Genetics, vol. 38, No. 3, pp. 105-112, Oct. 2000.
Chang et al., Characterization and Translational Regulation of the Arginine Decarboxylase Gene in Carnation (*Dianthus caryophyllus* L.), Plant Journal, vol. 24, No. 1, pp. 45-56, Oct. 2000.
Storchova et al., A Nicotiana Tabacum mRNA Encoding a 69-kDa Glycoprotein Occurring Abundantly in Pollen Tubes is Transcribed but not Translated During Pollen Development in the Anthers, Planta, vol. 192, No. 3, pp. 441-445, 1994.
Honys et al., Translational Regulation of Pollen Tube-Wall Specific Glycoprotein P69, Plant Physiology and Biochemistry, vol. 38, Supplement, p. 63, Aug. 2000.
Ow et al., Transient and Stable Expression of the Firefly Luciferase Gene in Plant Cells and Transgenic Plants, Science, vol. 234, pp. 856-859, 1986.
Topfer et al., A Set of Plant Expression Vectors for Transcriptional and Translational Fusions, Nucleic Acids Research, vol. 15, No. 14, p. 5890, 1987.
Weterings et al., Characterization of a Pollen-Specific cDNA Clone from Nicotiana Tabacum Expressed During Microgametogenesis and Germination, Plant Molecular Biology, vol. 18, pp. 1101-1111, 1992.
Weterings et al., Dynamic 1-Aminocyclopropane-1-Carboxylate-Synthase and -Oxidase Transcript Accumulation Patterns During Pollen Tube Growth in Tobacco Styles, Plant Physiology, vol. 130, pp. 1190-1200, 2002.
Weterings et al., Functional Dissection of the Promoter of the Pollen-Specific Gene NTP303 Reveals a Novel Pollen-Specific, and Conserved Cis-Regulatory Element, The Plant Journal, vol. 8, pp. 55-63, 1995.
Weterings et al., Molecular Characterization of the Pollen-Specific Genomic Clone NTPg303 and In Situ Localization of Expression, Sexual Plant Reproduction, vol. 8(1), pp. 11-17, 1995.
Xu et al., Isolation and Characterization of Male-Germ-Cell Transcripts in Nicotiana Tabacum, Sexual Plant Reproduction, vol. 14, pp. 339-346, 2002.

(Continued)

*Primary Examiner* — Li Zheng
(74) *Attorney, Agent, or Firm* — McDonnell Boehnen Hulbert & Berghoff LLP

(57) ABSTRACT

The present invention pertains to a method of expressing a protein of interest, preferably a heterologous protein, in preferably a plant. In a preferred embodiment said plant is a doubled haploid homozygous transgenic *Nicotiana tabacum* plant silenced for Ntp303. Furthermore, the invention relates to said plant with or without nucleic acid constructs according to the invention. Propagation, harvest and tissue material of said transgenic *Nicotiana tabacum* plant is also a part of the invention.

17 Claims, 10 Drawing Sheets

(56) References Cited

OTHER PUBLICATIONS

Pesole et al., Structural and Functional Features of Eukaryotic mRNA Untranslated Regions, Gene, vol. 276, pp. 73-81, 2001.
Bailey-Serres, Selective Translation of Cytoplasmic mRNAs in Plants, Trends in Plant Science, vol. 4, pp. 142-148, 1999.
Bate et al., Maturation-Specific Translational Enhancement Mediated by the 5'-UTR of a Late Pollen Transcript, Plant Journal, vol. 10, pp. 613-623, 1996.
Burd et al., Conserved Structures and Diversity of Functions of RNA-Binding Proteins, Science, vol. 265, pp. 615-621, Jul. 29, 1994.
Edwards et al., Cell-Specific Gene Expression in Plants, Annu. Rev. Genet., vol. 24, pp. 275-303, 1990.
Hamilton et al., Dissection of a Pollen-Specific Promoter from Maize by Transient Transformation Assays, Plant Molecular Biology, vol. 18, pp. 211-218, 1992.
Van Herpen et al., In-Vitro Culture of Tobacco Pollen: Gene Expression and Protein Synthesis, Sexual Plant Reproduction, vol. 5, pp. 304-309, 1992.
Hofacker et al., Fast Folding and Comparison of RNA Secondary Structures, Chemical Monthly, vol. 125, pp. 167-188, 1994.
Jefferson et al., GUS Fusions: β-glucuronidase as a Sensitive and Versatile Gene Fusion Marker in Higher Plants, The EMBO Journal, vol. 6, pp. 3901-3907, 1987.
Murray et al., Codon Usage in Plant Genes, Nucleic Acids Research, vol. 17, No. 2, pp. 477-498, 1989.
Read et al., Stimulation of Growth of Cultured Nicotiana tabacum W38 Pollen Tubes by Poly(ethylene glycol) and CU(II) Salts, Protoplasma, vol. 177, pp. 1-14, 1993.
Schrauwen et al., Mass Culture of Pollen Tubes, Acta Botanica Neerlandica, vol. 16(5), pp. 177-179, Nov. 1967.
Tupy et al., Production of Fertile Tobacco Pollen from Microspores in Suspension Culture and its Storage for In Situ Pollination, Sexual Plant Reproduction, vol. 4, pp. 284-287, 1991.
International Search Report dated May 20, 2003 for PCT Application No. PCT/NL2002/000638.
Written Opinion dated Jul. 9, 2003 for PCT Application No. PCT/NL2002/000638.
International Preliminary Examination Report dated Dec. 29, 2003, for PCT Application No. PCT/NL2002/000638.
Communication from the Examining Division dated Aug. 28, 2006 for European Application No. EP2002763110.
Response to Communication from the Examining Division dated Dec. 12, 2006 for European Application No. EP2002763110.
Communication from the Examining Division dated Apr. 20, 2007 for European Application No. EP2002763110.
Response to Communication from the Examining Division dated Aug. 2, 2007 for European Application No. EP2002763110.
Summons to Attend Oral Proceedings dated Apr. 8, 2008 for European Application No. EP2002763110.
Response to Summons dated Jun. 18, 2008 for European Application No. EP2002763110.
Communication from the Examining Division dated Jul. 3, 2008 for European Application No. EP2002763110.
Response to Communication from the Examining Division dated Dec. 16, 2008 for European Application No. EP2002763110.
Communication from the Examining Division dated Jan. 12, 2009 for European Application No. EP2002763110.
Response to Communication from the Examining Division dated Feb. 16, 2009 for European Application No. EP2002763110.
Summons to Attend Oral Proceedings dated Aug. 18, 2009 for European Application No. EP2002763110.
Response to Summons dated Sep. 28, 2009 for European Application No. EP2002763110.
Response to Summons dated Oct. 8, 2009 for European Application No. EP2002763110.
Record of Consultation dated Oct. 9, 2009 for European Application No. EP2002763110.
Intent to Grant Letter dated Nov. 26, 2009 for European Application No. EP2002763110.
Request for Further Processing and Amended Claims dated Jul. 16, 2010 for European Application No. EP2002763110.
Communication from the Examining Division dated Oct. 22, 2010 for European Application No. EP2002763110.
Preliminary Amendment dated Apr. 5, 2004 for U.S. Appl. No. 10/491,749.
Restriction Requirement dated Sep. 8, 2006 for U.S. Appl. No. 10/491,749.
Response to Restriction Requirement dated Dec. 8, 2006 for U.S. Appl. No. 10/491,749.
Restriction Requirement dated Mar. 7, 2007 for U.S. Appl. No. 10/491,749.
Response to Restriction Requirement dated Jun. 7, 2007 for U.S. Appl. No. 10/491,749.
Non-Final Office Action dated Sep. 18, 2007 for U.S. Appl. No. 10/491,749.
Response to Non-Final Office Action dated Mar. 18, 2008 for U.S. Appl. No. 10/491,749.
Response to Non-Final Office Action dated Apr. 7, 2008 for U.S. Appl. No. 10/491,749.
Final Office Action dated Jul. 9, 2008 for U.S. Appl. No. 10/491,749.
Response to Final Office Action dated Jan. 8, 2009 for U.S. Appl. No. 10/491,749.
Supplemental Response to Final Office Action dated Jan. 23, 2009 for U.S. Appl. No. 10/491,749.
Notice of Allowance dated Oct. 23, 2009 for U.S. Appl. No. 10/491,749.
Notice of Allowance dated Feb. 22, 2010 for U.S. Appl. No. 10/491,749.
Notice of Withdrawal from Issue dated Jul. 29, 2010 for U.S. Appl. No. 10/491,749.
Notice of Allowance dated Sep. 28, 2010 for U.S. Appl. No. 10/491,749.
Hulzink et al, Plant Physiology, vol. 129, No. 129, 2002, pp. 342-353.
Chappell, Ribosomal tethering and clustering as mechanisms for translation initiation (2006) 103, pp. 18077-18082.
Chen et al., RNA secondary structure and compensatory evolution, Genes Genet. Syst. (1999) 74, pp. 271-286.
Costello et al., Global mRNA selection mechanisms for translation initiation, Genome Biology (2015) 16, pp. 1-21.
De Breyne et al., Direct functional interaction of initiation factor eIF4G with type 1 internal ribosomal entry sites, PNAS (2009) 106, pp. 9197-9202.
Jackson et al., The mechanism of eukaryotic translation initiation and principles of its regulation, Molecular Cell Biology (2010) 10, pp. 113-127.
Jang et al., Cap-dependent translation is mediated by 'RNA looping' rather than 'ribosome scanning', RNA Biology (2016) 13, pp. 1-15.
Jang et al., A Segment of the 5' Nontranslated Region of Encephalomyocarditis Virus RNA Directs Internal Entry of Ribosomes during In Vitro Translation, Journal of Virology (1988), pp. 2636-2643.
Kisselev et al., Translational termination comes of age, Trends in Biochem. Sci. (2000) 25, pp. 561-566.
Kozak, Circumstances and Mechanisms of Inhibition of Translation by Secondary Structure in Eucaryotic mRNAs, Molecular and Cellular Biology (1989), pp. 5134-5142.
Ladner et al., Structure of yeast phenylalanine transfer RNA at 2.5 Å resolution, Proc. Nat. Acad. Sci. USA (1975) 72, pp. 4414-4418.
Mathews et al., Expanded Sequence Dependence of Thermodynamic Parameters Improves Prediction of RNA Secondary Structure, J. Mol. Biol. (1999) 288, pp. 911-940.
Nottrott et al., Functional Interaction of a novel 15.5kD [U4/U6•U/5] tri-snRNP protein with the 5' stem-loop of U4 snRNA, Eur. Mol. Bio. Org. Journal (1999) 18, pp. 6119-6133.
Paek et al., Translation initiation mediated by RNA looping, PNAS (2105) 112, pp. 1041-1046.
Phillips et al., Identification of a stem-loop structure important for polyadenylation at the murine IgM secretory poly(A) site, Nuc. Acid. Res. (1999) 27, pp. 429-438.

(56) References Cited

OTHER PUBLICATIONS

Smith et al., Sno Storm in the Nucleolus: New Roles for Myriad Small RNPs, Cell (1997) 89, pp. 669-672.
Tam, Identification and characterization of human BIC, a gene on chromosome 21 that encodes a noncoding RNA, Gene (2001) 274, pp. 157-167.
Zuker, Mfold web server for nucleic acid folding and hybridization prediction, Nuc. Acid. Res. 2003, 31, pp. 3406-3415.

* cited by examiner

SEQUENCE LISTING

```
<160> NUMBER OF SEQ ID NOS: 20

<210> SEQ ID NO 1
<211> LENGTH: 173
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 1
caagctctag caggaagaag aaataagaag aagaagaaga agaagaagaa gcgtctcctc        60
ttcttcttgt gagagtaaaa aataaaactc ccaaaaaaaa gaaaatcatc aaaaaaacaa       120
atttcaaaaa gagttttgt gtttggggat taaagaataa aaaaaacaac gtc              173

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 2
atatccatgg aagacgcc                                                      18

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 3
atatggatcc ttacacggcg atc                                                23
```

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: note = synthetic construct

<400> SEQUENCE: 4
gtgtccatgg atgacttcga aag                                          23

<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: note = synthetic construct

<400> SEQUENCE: 5
gtgtggatcc ttattgttca tttttgag                                     28

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: note = synthetic construct

<400> SEQUENCE: 6
gtgtctcgag caagctctag caggaag                                      27

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: note = synthetic construct

<400> SEQUENCE: 7
gtgtccatgg gacgttgttt tttttattc                                    29

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: note = synthetic construct

<400> SEQUENCE: 8
atatggatcc attctgtaat gatcaatctg                                   30

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: note = synthetic construct

<400> SEQUENCE: 9
atatgagctc atttaatgtt ttgtccta                                     28

```
<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 10
atataagctt gatacactcg caacgtgtgt                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 11
atatctcgag gagcttgcac tattcaccat                                    30

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 12
gtgtctcgag ttgcaattgg atcc                                          24

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 13
gtgtccatgg ccgcggg                                                  17

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 14

Ser Xaa Xaa Xaa Xaa Arg Lys Xaa Lys
1               5

<210> SEQ ID NO 15
<211> LENGTH: 148
<212> TYPE: DNA
<213> ORGANISM: Artificial Sequence
```

```
<220> FEATURE:
<223> OTHER INFORMATION: Description of Artificial Sequence: note =
      synthetic construct

<400> SEQUENCE: 15
agaagaagaa gaagaagaag aagaagcgtc tcctcttctt cttgtgagag taaaaaataa     60
aactcccaaa aaaagaaaaa tcatcaaaaa aacaaatttc aaaagagtt tttgtgtttg     120 gggattaaag aataaaaaaa acaacgtc                                        148

<210> SEQ ID NO 16
<211> LENGTH: 122
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 16
cgtctcctct tcttcttgtg agagtaaaaa ataaaactcc caaaaaaag aaaatcatca     60 aaaaaacaaa tttcaaaaag agttttttgtg tttggggatt aaagaataaa aaaaacaacg   120
tc                                                                    122

<210> SEQ ID NO 17
<211> LENGTH: 148
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 17
caagctctag caggaagaag aaataacgtc tcctcttctt cttgtgagag taaaaaataa     60
aactcccaaa aaaagaaaaa tcatcaaaaa aacaaatttc aaaagagtt tttgtgtttg     120 gggattaaag aataaaaaaa acaacgtc                                        148

<210> SEQ ID NO 18
<211> LENGTH: 173
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 18
caagctctag caggaagaag aaataagaag aagaagaaga agaagaagaa gcgtctcctc     60
ttcttcttgt gagagtaaaa aataaaactc ccaaaaaaaa gaaaatcatc aaaaaaacaa    120
atttcaaaaa gagttttttgt gtttggggat taaagaataa aaaaaacaac gtc          173

<210> SEQ ID NO 19
<211> LENGTH: 103
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 19
caagctctag caggaagaag aaataagaag aagaagaaga agaagaagaa gcgtctcctc     60
ttcttcttgt gagagtaaaa aataaaactc ccaaaaaaaa gaa                      103
```

```
<210> SEQ ID NO 20
<211> LENGTH: 125
<212> TYPE: DNA
<213> ORGANISM: Artificial Sequence
<220> FEATURE:
<223> OTHER INFORMATION: Description of Artificial Sequence: note =
      synthetic construct

<400> SEQUENCE: 20
caagctctag caggaagaag aaataagaag aagaagaaga agaagaagaa gcgtctcctc        60
ttcttcttgt gagagtaaaa aataaaactc ccaaaaaaaa gaaaaagaat aaaaaaaaca       120
acgtc                                                                   125
```

REGULATION OF TRANSLATION OF HETEROLOGOUSLY EXPRESSED GENES

CROSS-REFERENCE TO RELATED PATENT APPLICATIONS

This application claims priority to U.S. patent application Ser. No. 10/491,749 filed on Apr. 5, 2004, which is national phase application of International Application No. PCT/NL02/00638 filed on Oct. 4, 2002, which claims priority to U.S. patent application Ser. No. 60/327,003 filed on Oct. 5, 2001, to EP 01203772.7 filed on Oct. 5, 2001, and to EP 02076593.9 filed Apr. 19, 2002, all of which are hereby incorporated herein by reference in their entireties.

BACKGROUND OF THE INVENTION

Sexual reproduction in plants and animals requires the production of gametes. Although many cytological differences exist in the developmental stages of gamete development between the plant and animal kingdoms, several parallels exist. In plants as well as in animals, gamete production is a highly ordered process characterised by transitions of stem cells from one physiological state to the next by mitotic and meiotic divisions. These series of events are directed by multiple changes in gene expression. Several stages in gamete development in several plant and animal species proceed almost without any transcriptional activity. In these stages, previously synthesised mRNAs are translated into products that are essential for further development. This implies that, in these species, post-transcriptional control of gene expression is the leading principle in gamete development. An example of post-transcriptional regulation of gene expression during gamete development is the maturation and germination of the male gametophyte (pollen) in angiosperm plants. Immature pollen consists of a small generative cell and a large vegetative cell which are formed out of microspores through an asymmetric haploid mitotic division (pollen mitosis 1). During the subsequent stages in development some species have a second haploid mitosis (pollen mitosis II) resulting in tricellular pollen, a process absent in most species (i.e. bicellular pollen). Maturation of this bi- and tricellular pollen is completed by a range of developmental processes which finally result in a progressive dehydration of the pollen and its transition to dormancy. Maturation of pollen of several plant species is accompanied by an accumulation of large quantities of rRNAs, tRNAs, mRNAs and ribosomes. As soon as the pollen lands on a compatible stigma, an extensive rehydration of the pollen grain occurs leading to a rapid reactivation of the translation machinery which uses the previously accumulated tRNAs, rRNAs and mRNAs. The proteins that are synthesized from these stored products are required for the progamic life stage of the pollen, i.e. germination of the pollen, the subsequent growth of the pollen tube and the second haploid mitosis in case of the bicellular pollen.

Despite the importance of post-transcriptional processes for the regulation of pollen gene expression, little is known about the mechanisms underlying post-transcriptional regulation of pollen gene expression. There is only one study in the art that focuses on the translational regulation of a pollen expressed gene (lat52) (Bate et al., (1996) Plant J., 10(4), 613-623). In this study, the involvement of the 5' UTR in the pollen specific regulation of translation has been demonstrated. More in general, the rate of translation is influenced by cis-acting elements in mRNAs. E.g. the translation level of mRNA species from different eukaryotic systems is modulated by cis-acting elements in the 5' UTR, the coding sequence, or the 3' UTR. These cis-acting elements act by influencing mRNA stability, translation initiation or elongation.

The regulation of the synthesis of the tobacco pollen protein NTP303 takes place at the post-transcriptional level. Transcripts of the ntp303 gene are first detectable after pollen mitosis I and continue to accumulate during pollen maturation and subsequent pollen tube growth (Weterings et al., (1992) Plant Mol. Bioi. 18(6), 1101-1111). In contrast, the protein only appears in detectable amounts at the onset of pollen rehydration (Wittink et al., (2000) Sex. Plant Reprod. 12(5), 276-284). Thus, despite the accumulation of its mRNA there is no efficient synthesis of the NTP303 protein during pollen development, which constraint is only relieved at the onset of pollen germination. It is, however, not clear what cis-acting elements in the npt303 mRNA, if any, are responsible for this mechanism of translational regulation. In particular it is not clear whether any such elements could be used to regulate the expression of proteins other than NPT303, such as heterologous proteins.

DESCRIPTION OF THE FIGURES

FIG. 7: Schematic representations and expression effects of ntp303 5' UTR H-I (A and B) and H-II (C and D) mutations. FIG. 7B and FIG. 7D reflect the effect of the constructs of FIG. 7A and FIG. 7C, respectively, upon the pollen tube growth. Rlu/10 sec.$^{-1}$ means the relative light units per 10 seconds measuring time as determined by normalization of the absolute expression of the test construct with that of the reference construct. Measurements were assayed after 20 hours of pollen tube growth.

DESCRIPTION OF THE INVENTION

Definitions

Figure 1:
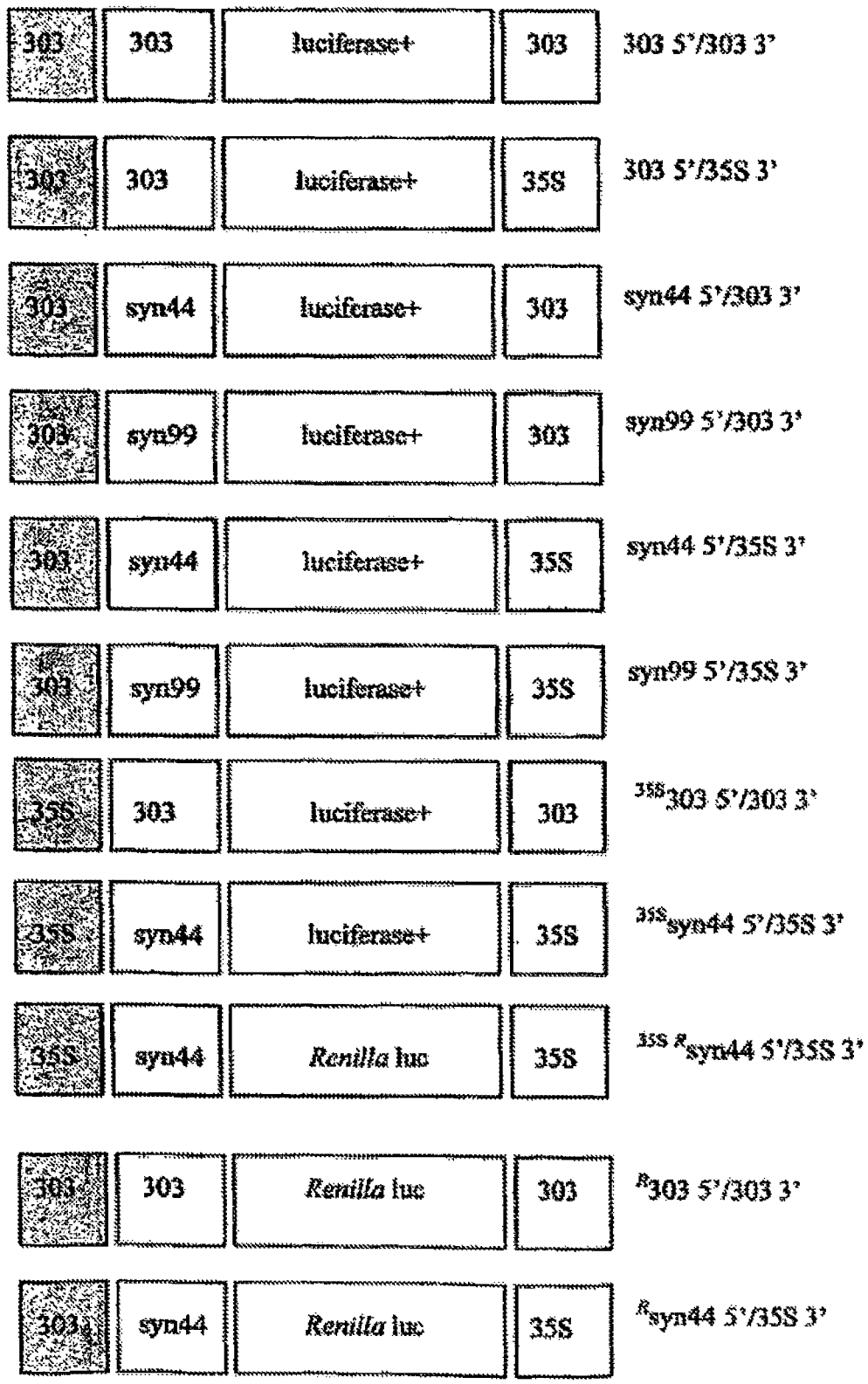
FIG. 1: Schematic representation and names of the UTR gene fusion constructs used in the present study.

Herebelow follow definitions of terms as used in the invention.

Plant

As used herein, the term "plant" refers to either a whole plant, including in general the class of higher plants amenable to transformation techniques, including both monocotyledonous and dicotyledonous plants or a part of a plant such as e.g. roots, stems, stalks, leaves, petals, fruits, seeds, tubers, pollen, meristems, callus, sepals, bulbs and flowers. The term plant as used herein further refers, without limitations, to plant cells in seeds, suspension cultures, embryos, meristematic regions, callus tissue, leaves, roots, shoots, gametophytic and sporophytic tissue, pollen, protoplasts and microspores. Furthermore, all plant tissues in all organs are included in the definition of the term plant as used herein. Plant tissues include, but is not limited to, differentiated and undifferentiated tissues of a plant, including pollen, pollen tubes, pollen grains, roots, shoots, shoot meristems, coleoptilar nodes, tassels, leaves, cotyledonous petals, ovules, tubers, seeds, kernels. Tissues of plants may be in planta, or in organ, tissue or cell culture. As used herein, monocotyledonous plant refers to a plant whose seeds have only one cotyledon, or organ of the embryo that stores and absorbs food. As used herein, dicotyledonous plant refers to a plant whose seeds have two cotyledons. Plants included in the invention are all plants amenable to transformation.

Operably Linked

As used herein, the term "operably linked" refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

Promoter

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one skilled in the art to act directly or indirectly to regulate the amount of transcription from the promoter.

Hybridising Nucleic Acid Orthologs and Hybridising 5' UTRs

Any nucleotide sequence capable to hybridise to the nucleotide sequences of SEQ ID NO. 1 is defined as being part of the 5' UTR of the invention. Stringent hybridisation conditions are herein defined as conditions that allow a nucleic acid sequence of at least 25, preferably 50, 75 or 100, and most preferably 150 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity. Moderate hybridization conditions are herein defined as conditions that allow a nucleic acid sequence of at least 50, preferably 150 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

Homologous

The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically be operably linked to another promoter sequence or, if applicable, another secretory signal sequence and/or terminator sequence than in its natural environment.

When used to indicate the relatedness of two nucleic acid sequences the term "homologous" means that one single-stranded nucleic acid sequence may hybridise to a complementary single-stranded nucleic acid sequence. The degree of hybridisation may depend on a number of factors including the extent of identity between the sequences and the hybridisation conditions such as temperature and salt concentration as discussed later. Preferably the region of identity is greater than 5 bp, more preferably the region of identity is greater than 10 bp.

Heterologous

The term "heterologous" when used with respect to a nucleic acid or polypeptide molecule refers to a nucleic acid or polypeptide from a foreign cell which does not occur naturally as part of the organism, cell, genome or DNA or RNA sequence in which it is present, or which is found in a cell or location or locations in the genome or DNA or RNA sequence that differ from that in which it is found in nature. Heterologous nucleic acids or proteins are not endogenous to the cell into which they are introduced, but have been obtained from another cell or synthetically or recombinantly produced. Generally, though not necessarily, such nucleic acids encode proteins that are not normally produced by the cell in which the DNA is transcribed or expressed, similarly exogenous RNA codes for proteins not normally expressed in the cell in which the exogenous RNA is present. Furthermore, it is known that a heterologous protein or polypeptide can be composed of homologous elements arranged in an order and/or orientation not normally found in the host organism, tissue or cell thereof in which it is transferred, i.e. the nucleotide sequence encoding said protein or polypeptide originates from the same species but is substantially modified from its native form in composition and/or genomic locus by deliberate human intervention. Heterologous nucleic acids and proteins may also be referred to as foreign nucleic acids or proteins. Any nucleic acid or protein that one of skill in the art would recognise as heterologous or foreign to the cell in which it is expressed is herein encompassed by the term heterologous nucleic acid or protein. The term heterologous also applies to non-natural combinations of nucleic acid or amino acid sequences, i.e. combinations where at least two of the combined sequences are foreign with respect to each other.

Sequence Identity

"Sequence identity", as known in the art, is a relationship between two or more amino acid (polypeptide or protein) sequences or two or more nucleic acid (polynucleotide) sequences, as determined by comparing the sequences. In the art, the percentage of "identity" indicates the degree of sequence relatedness between amino acid or nucleic acid sequences as determined by the match between strings of such sequences. Two amino acid sequences are considered "similar" if the polypeptides only differ in conserved amino acid substitutions. In determining the degree of amino acid similarity, the skilled person takes into account "conservative" amino acid substitutions. Conservative amino acid substitutions refer to the interchange of amino acids having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleuci-ne, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; Asn to gln or glu; Met to leu or ile; Phe to met, leu or tyr; Ser to thr; Thr to ser; Trp to tyr; Tyr to trp or phe; and, Val to ile or leu.

"Identity" and "similarity" can be readily calculated by known methods, including but not limited to those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heine, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48:1073 (1988).

Preferred methods to determine identity are designed to give the largest match between the sequences tested. Methods to determine identity and similarity are codified in publicly available computer programs. Preferred computer program methods to determine identity and similarity between two sequences include e.g. the GCG program package (Devereux, J., et al., Nucleic Acids Research 12 (1):387 (1984)), BestFit and PASTA (Altschul, S. F. et al., J. Mol. Biol. 215:403-410 (1990). The BLAST 2.0 family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. The BLASTX program is publicly available from NCBI and other sources (BLAST Manual, Altschul, S., et al., NCBI NLM NIH Bethesda, Md. 20894; Altschul, S., et al., J. Mol. Biol. 215:403-410 (1990)). The well-known Smith Waterman algorithm may also be used to determine identity.

Preferred parameters for polypeptide sequence comparison include the following: Algorithm: Needleman and Wunsch, J. Mol. Biol. 48:443-453 (1970); Comparison matrix: BLOSSUM62 from Hentikoff and Hentikoff, Proc. Natl. Acad. Sci. USA. 89:10915-10919 (1992); Gap Penalty: 12; and Gap Length Penalty: 4. A program useful with these parameters is publicly available as the "Ogap" program from Genetics Computer Group, located in Madison, Wis. The aforementioned parameters are the default parameters for amino acid comparisons (along with no penalty for end gaps).

Preferred parameters for nucleic acid comparison include the following: Algorithm: Needleman and Wunsch, J. Mol. Biol. 48:443-453 (1970); Comparison matrix: matches=+10, mismatch=0; Gap Penalty: 50; Gap Length Penalty: 3. Available as the Gap program from Genetics Computer Group, located in Madison, Wis. Given above are the default parameters for nucleic acid comparisons.

Ligand

As used herein, the term "ligand" refers to an agent that specifically binds to a target RNA, preferably mRNA. As used herein the term "specific binding" means binding that is measurably different from a non-specific interaction. Specific binding can be measured, for example, by determining binding of an agent compared to binding of a control agent, which generally is an agent of similar structure that does not have binding activity, for example a RNA molecule of similar size that lacks a specific binding sequence. Specific binding is present if the agent has measurably higher affinity for the target RNA than the control agent. Specificity of binding can be determined, for example, by competition with a control agent that is known to bind to a target. E.g., specific binding of an agent can be demonstrated by competing for binding with the same agent or a different agent specifically binding to the target RNA. Specific binding can be indicated if the binding of a molecule is competitively inhibited by the second agent. The term "specific binding" as used herein, includes both low and high affinity specific binding. Specific binding can be exhibited, e.g. by a low affinity binding agent having a Kd of at least about 1 mM and higher. Specific binding can also be exhibited by a high affinity binding agent having a Kd of at least about 1 µM and lower: The difference between a high and low affinity binding agent is about a factor 1,000. The agent may bind the target RNA when the target RNA is in a native or alternative conformation, or when it is partially or totally unfolded or denatured. According to the present invention, a ligand can be an agent that binds anywhere on the target RNA, but preferably the ligand binds on the indicated nucleotide sequences of the target RNA. Ligands can be virtually any agent, including without limitation metals, peptides, proteins, lipids, polysaccharides, small organic molecules, nucleotides (including non-naturally occurring ones) and combinations thereof Messenger RNA "Messenger RNA (mRNA)" as used herein refers to a temporary complementary copy of RNA of the antisense strand (anticoding strand or template) of protein coding DNA. In eukaryotes it is usually transcribed as a relatively long pre-mRNA (also called primary transcript or hnRNA) which is then processed, still within the nucleus, to remove introns. Further post-transcriptional modifications can also occur. The mature mRNA is then transported into the cytoplasm where it is translated into protein on the ribosome. Furthermore, an mRNA generally comprises a region that specifies the protein sequence, flanked on either side by untranslated regions called 5' and 3' untranslated regions (5'UTR and 3'UTR).

Antisense Nucleic Acid

"Antisense nucleic acid" as used herein refers to a RNA, DNA or PNA molecule that is complementary to all or part of a target primary transcript or mRNA and that blocks the translation of a target nucleotide sequence.

DETAILED DESCRIPTION OF THE INVENTION

As a first aspect, the invention relates to a method for expressing a protein or polypeptide of interest in a plant comprising the steps of:

a) providing a nucleic acid construct comprising a first nucleotide sequence that has at least 34% nucleotide sequence identity with the nucleotide sequence of SEQ ID No. 1, operably linked to a second nucleotide sequence encoding a protein or polypeptide of interest and further operably linked to a heterologous promotor, b) contacting a plant with said nucleic acid construct to obtain a transformed plant, and c) subjecting said transformed plant to conditions leading to expression of the protein or polypeptide of interest, and optionally recovering said protein or polypeptide.

According to the invention the nucleic acid construct comprises a first nucleotide sequence that has at least 34% nucleotide sequence identity to the nucleotide sequence of SEQ ID No. 1 (using the BLAST algorithm of BLASTN 2.2.1; 13-04-2001; gap penalties: existence 5, extension 2). The nucleic acid construct according to the invention preferably comprises a first nucleotide sequence that has at least 36%, more preferably at least 40%, 45%, 50%, 55%, 60%, 65%, 70%, 75%, 80%, 85%, 90%, 95% or 98% nucleotide sequence identity to the nucleotide sequence of SEQ ID No. 1. In a particularly preferred embodiment of the invention the nucleic acid construct comprises a first nucleotide sequence that has 100% nucleotide sequence identity to the nucleotide sequence of SEQ ID No. 1. The nucleotide sequence presented herein as SEQ ID No. 1 is the 5' UTR sequence of the ntp303 gene of Nicotiana tabacum.

In a further embodiment the invention relates to a method for expressing a protein of interest in a plant comprising the steps of:

a) providing a nucleic acid construct comprising a first nucleotide sequence comprising a nucleotide sequence that has at least 46% nucleotide sequence identity to nucleotides 104-151 of the nucleotide sequence of SEQ ID No. 1 or a nucleotide sequence that has at least 51% nucleotide sequence identity to nucleotides 4-76 of the nucleotide sequence of SEQ ID No. 1 or a combination thereof, operably linked to a second nucleotide sequence encoding a protein or polypeptide of interest and further operably linked to a heterologous promotor, b) contacting a plant with said nucleic acid construct to obtain a transformed plant, and c) subjecting said transformed plant to conditions leading to expression of the protein or polypeptide of interest, and optionally recovering said protein or polypeptide.

Preferably, said first nucleotide sequence comprises a nucleotide sequence that has at least 48%, 50%, 55%, 60%, 65%, 70%, 75%, 80%, 85%, 90%, 95%, 98% and particularly 100% nucleotide sequence identity to nucleotides 104-151 of the nucleotide sequence of SEQ ID No. 1 or a nucleotide sequence that has at least 55%, more preferably at least 60%, 65%, 70%, 75%, 80%, 85%, 90%, 95%, 98% and particularly 100% nucleotide sequence identity to nucleotides 4-76 of the nucleotide sequence of SEQ ID No. 1 or a combination thereof.

In another embodiment of the above mentioned method the first nucleotide sequence comprises a nucleotide sequence that has at least 46%, 48%, 50%, 55%, 60%, 65%, 70%, 75%, 80%, 85%, 90%, 95%, 98% and particularly 100% nucleotide sequence identity to nucleotides 104-151 of the nucleotide sequence of SEQ ID No. 1 or a nucleotide sequence that has 100% nucleotide sequence identity to nucleotides 27-50 of the nucleotide sequence of SEQ ID No. 1 or a combination thereof. The nucleotides 27-50 of the nucleotide sequence of SEQ ID No. 1 consist of a repeat of 8 GAA-units. Preferably, said first nucleotide sequence comprises a nucleotide sequence that consists of 7, 6, 5, 4 or 3 GAA units.

A nucleotide sequence according to the invention can be present in the form of RNA or in the form of DNA including genomic DNA, i.e. DNA including the introns, cDNA or synthetic DNA. The DNA may be double-stranded or single-stranded and if single-stranded may be the coding strand or non-coding (anti-sense) strand. DNA or RNA with a backbone modified for stability or for other reasons are a further part of the invention. Moreover, DNA or RNA comprising unusual bases, such as inosine, or modified bases, such as tritylated bases are also a part of the invention. The nucleotide sequence may also be a allelic variant of the nucleotide sequence according to the invention. If desired, the nucleotide sequence can be prepared or altered synthetically so the known codon preferences of the intended expression host can advantageously be used. It has been shown for instance that the codon preferences and GC content preferences of monocotyledons and dicotyledons differ (Murray et al., Nucl. Acids Res. 17: 477498 (1989)).

In a preferred embodiment of the method according to the invention the nucleic acid construct comprises a second nucleotide sequence encoding a protein or polypeptide of interest that is operably linked to any one of the first nucleotide sequences as defined above. The protein or polypeptide of interest can be a homologous protein or polypeptide, but in a preferred embodiment of the invention the protein or polypeptide of interest is a heterologous protein. A second nucleotide sequence encoding a heterologous protein or polypeptide may be derived in whole or in part from any source known to the art, including a bacterial or viral genome or episome, eukaryotic nuclear or plasmid DNA, cDNA or chemically synthesised DNA. The second nucleotide sequence may constitute an uninterrupted coding region or it may include one or more introns bounded by appropriate splice junctions, it can further be composed of segments derived from different sources, naturally occurring or synthetic. The second nucleotide sequence encoding the protein or polypeptide of interest according to the method of the invention is preferably a full-length nucleotide sequence, but can also be a functionally active part or other part of said full-length nucleotide sequence. The protein or polypeptide of interest may be a protein or polypeptide conferring, for instance, insect resistance, drought resistance, disease resistance, herbicide resistance, immunity, an improved intake of nutrients, minerals or water from the soil, or a modified metabolism in the plant. In another embodiment the plant is used for overproduction of the protein or polypeptide of interest. The second nucleotide sequence encoding the protein or polypeptide of interest may also comprise signal sequences directing the protein or polypeptide of interest when expressed to a specific location in the cell or tissue. Such signal sequences include, but are not limited to, sequences directing the protein or polypeptide of interest to organelles, other plant cells or intercellular space. Furthermore, the second nucleotide sequence encoding the protein or polypeptide of interest can also comprise sequences which facilitate protein purification and protein detection by for instance Western blotting and ELISA (e.g. c-myc or polyhistidine sequences).

The protein or polypeptide of interest may have industrial or medicinal (pharmaceutical) applications. Examples of proteins or polypeptides with industrial applications include enzymes such as e.g. lipases (e.g used in the detergent industry), proteases (used inter alia in the detergent industry, in brewing and the like), cell wall degrading enzymes (such as, cellulases, pectinases, β-1,3/4- and β-1,6-glucanases, rhamnoga-lacturonases, mannanases, xylanases, pullulanases, galactanases, esterases and the like, used in fruit processing wine making and the like or in feed), phytases, phospholipases, glycosidases (such as amylases, (β-glucosidases, arabinofuranosidases, rhamnosidases, apiosidases and the like), dairy enzymes (e.g. chymosin). Mammalian, and preferably human, proteins or polypeptides and/or enzymes with therapeutic, cosmetic or diagnostic applications include, but are not limited to, insulin, serum albumin (HSA), lactoferrin, hemoglobin α and β, tissue plasminogen activator (tPA), erythropoietin (EPO), tumor necrosis factors (TNF), BMP (Bone Morphogenic Protein), growth factors (G-CSF, GM-CSF, M-CSF, PDGF, EGF, and the like), peptide hormones (e.g. calcitonin, somatomedin, somatotropin, growth hormones, follicle stimulating hormone (FSH) interleukins (IL-x), interferons (IFN-y). Also included are bacterial and viral antigens, e.g. for use as vaccines, including e.g. heat-labile toxin B-subunit, cholera toxin B-subunit, envelope surface protein Hepatitis B virus, capsid protein Norwalk virus, glycoprotein B Human cytomegalovirus, glycoprotein S, interferon, and transmissible gastroenteritis corona virusreceptors and the like. Further included are genes coding for mutants or analogues of the said proteins.

In an embodiment of the invention the nucleic acid construct further comprises a promotor for control and initiation of transcription of the second nucleotide sequence. The promoter preferably is capable of causing expression of the second nucleotide sequence in the host cell of choice. Said promoter, e.g. pollen-specific or heterologous, is operably linked to any one of the nucleotide sequences mentioned above. In a preferred embodiment of the invention the promoter is a plant promoter, i.e. a promoter capable of initiating transcription in plant cells. Plant promotors as used herein include tissue-specific, tissue-preferred, cell-type-specific, inducible and constitutive promoters. Tissue-specific promoters are promoters which initiate transcription only in certain tissues and refer to a sequence of DNA that provides recognition signals for RNA polymerase and/or other factors required for transcription to begin, and/or for controlling expression of the coding sequence precisely within certain tissues or within certain cells of that tissue. Expression in a tissue specific manner may be only in individual tissues or in combinations of tissues. In a preferred embodiment of the invention the expression is pollen or seed specific, i. e. the expression is specific to pollen or seeds only. Pollen-specific and seed-specific promoters include, but are not limited to, promotors of the pollen-specific genes ntp303 (*N. tabacum*) and zm13 (*Z. mays*) and the seed-specific genes dc8 (*D. carota*), rab17 (*Z. mays*), rab16b (*O. sativa*) and em (*T. aestivum*). The group of tissue-specific promoters are reviewed by Edwards, J. W. & Cornzzi, G. M., Annu Rev. Genet. 24, 275-303 (1990) and include, but are not limited to, embryo-specific promoters such as the promoters of the embryonic storage proteins soybean .beta.-conglycinin gene, legumin genes from common bean, .beta.phaseolin gene and napin and cruciferin genes from rapeseed, endosperm-specific promotors such as the promoters of maize zein genes, wheat glutenin genes and barley hordein genes, fruit-specific promoters such as the promotor of the tomato ethylene-responsive E8 gene, tuber-specific promoters such as the class-I patatin promoter of potato and leaf-specific promoters such as the promotors of ribulose-1,5-biphosphate carboxylase small subunit gene and the chlorophyll a/b binding protein gene.

Tissue-preferred promoters are promoters that preferentially initiate transcription in certain tissues, such as leaves, roots, stems, flowers or seeds.

Cell-type-specific promoters are promoters that primarily drive expression in certain cell types in one or more organs, for example, vascular cells in roots or leaves. Inducible promoters are promoters that are capable of activating transcription of one or more DNA sequences or genes in response to an inducer. The DNA sequences or genes will not be transcribed when the inducer is absent. Inducers known in the art include high salt concentrations, cold, heat or toxic elements and include pathogens or disease agents such as viruses. Or inducers can be chemical agents such as herbicides, proteins, growth regulators, metabolites or phenolic compounds. The inducer can also be an illumination agent such as darkness and light at various modalities including wavelength, intensity, fluence, direction and duration. Activation of an inducible promoter is established by application of the inducer. The group of generally inducible promotors includes, but is not limited to, the hsp70 heat shock promoter of *Drosphilia melanogaster*, a cold inducible promoter from *Brassica napus* and an alcohol dehydrogenase promoter which is induced by ethanol. Specific plant inducible promotors include, but are not limited to, the tetracycline-inducible promotor and the .alpha.-amylase promotor.

Constitutive promoters are promoters that are active under many environmental conditions and in many different tissue types. The group of constitutive promotors includes, but is not limited to, the 35S promotor or 19S promotor of the cauliflower mosaic virus (CaMV), the ubiquitin promotor, the coat promoter of TMV, the cassava vein mosaic virus promotors (CsVMV), the rice actin-I promoter and regulatory regions associated with *Agrobacterium* genes, such as nopaline synthase (Nos), mannopine synthase (Mas) or octopine synthase (Ocs).

The nucleic acid construct according to the invention is preferably a vector, in particular a plasmid, cosmid or phage or nucleotide sequence, linear or circular, of a single or double stranded DNA or RNA, derived from any source, in which a number of nucleotide sequences have been joined or recombined into a unique construction which is capable of introducing any one of the nucleotide sequences of the invention in sense or antisense orientation into a cell, in particular a plant cell. The choice of vector is dependent on the recombinant procedures followed and the host cell used. The vector may be an autonomously replicating vector or may replicate together with the chromosome into which it has been integrated. Preferably, the vector contains a selection marker. Useful markers are dependent on the host cell of choice and are well known to persons skilled in the art. In case the protein is to be obtained from leaves or roots, infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid. Suitable vectors which can be delivered using the presently known procedures include, but are not limited to, herpes simplex virus vectors, adenovirus vectors, papovavirus vectors (such as human papillomavirus vectors, polyomavirus vectors, SV40 vectors), adeno-associated virus vectors, retroviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book VIRAL VECTORS: GENE THERAPY AND NEUROSCIENCE APPLICATIONS (Ed. Caplitt and Loewy, 1995). *Agrobacterium*-based plasmid vectors are preferred for stable transformation of nucleic acid constructs in a plant genome. The choice of the transformation vector is dependent on the followed transformation procedure and the used host cell. Binary Ti vectors which can be used for *Agrobacterium*-mediated gene transfer include pBIN19, pC22, pGA482 and pPCV001.

A recombinant host cell, such as a mammalian (with the exception of human), plant, animal, insect, fungal or bacterial cell, containing one or more copies of a nucleic acid construct according to the invention is an additional subject of the invention. By host cell is meant a cell which contains a nucleic acid construct such as a vector and supports the replication and/or expression of the nucleic acid construct. Examples of suitable bacteria are Gram positive bacteria such as several species of the genera *Bacillus, Streptomyces* and *Staphylococcus* or Gram negative bacteria such as several species of the genera *Escherichia* and *Pseudomonas*. In the group of fungal cells preferably yeast cells are used. Expression in yeast can be achieved by using yeast strains such as *Pichia pastoris, Saccharomyces cerevisiae* and *Hansenula polymorpha*. Furthermore, insect cells such as cells from *Drosophila* and Sf9 can be used as host cells. Alternatively, a suitable expression system can be a baculovius system or expression systems using mammalian cells such as CHO, COS or Bowes melanoma cells. For transformation procedures in plants, suitable bacteria include *Agrobacterium tumefaciens* and *Agrobacterium rhizogenes*.

Another aspect of the invention relates to a plant that is genetically modified, preferably by the method of the invention, in that the plant comprises a nucleic acid construct as herein defined above. The nucleic acid construct preferably is a construct containing nucleic acid sequences that are manipulated or modified in vitro or at least ex plauta. As such, the nucleic acid construct preferably provides the plant with a combination of nucleic acid sequences which is not found in nature. The nucleic acid construct preferably is stably maintained, either as a autonomously replicating element, or, more preferably, the nucleic acid construct is integrated into the plant's genome, in which case the construct is usually integrated at random positions in the plant's genome, for instance by nonhomologuous recombination. Plants that are preferred in the invention include tobacco, potato, sugar, beet, soja, maize, rice, lupin, alfalfa, *Arabidopsis* and *Brassica*. Stably transformed (transgenic) plants or plant cells are produced by known methods. The term stable transformation refers to exposing plants, tissues or cells thereof to methods to transfer and incorporate foreign DNA into the plant genome. These methods include, but are not limited to, *Agrobacterium tumefaciens*-mediated gene transfer, transfer of purified DNA via microparticle bombardment, electroporation of protoplasts and microinjection or use of silicon fibers to facilitate penetration and transfer of DNA into the plant cell. Dicotyledonous plants are most frequently transformed by *Agrobacterium*-mediated gene transfer such as for instance by co-culture of regenerating plant protoplasts or cell cultures with *Agrobacterium tumefaciens*. In general, when *Agrobacterium tumefaciens* is used for transformation, the transformation vectors are preferably cointigrating vectors or binary vectors. Dicotyledonous plants can furthermore be transformed by transformation of leaf discs, by protoplast transformation by polyethylene glycol-induced DNA transfer, electroporation, sonication or microinjection as well as transformation of intact cells or tissues by micro- or macroinjection into tissues or embryos, tissue electroporation, incubation of dry embryos in DNA-containing solution, vacuum infiltration of seed and biolistic gene transfer. Monocotyledonous plants are transformed via for example particle bombardment, electrically or chemically induced DNA incorporation into protoplasts, electroporation of partially permeabilized cells, macroinjection of DNA into inflorescences, microinjection of DNA into microspores and pro-embryos, the introduction of DNA into germinating pollen and DNA integration into embryos by swelling.

An alternative method to express a protein or polypeptide of interest in plants relies on transient expression from virus-based vectors. It is known that viruses replicate with high efficiency and, in some cases, can infect the entire host plant, creating the potential to express a protein or polypeptide of alternative method are tobamovirus, potexvirus and potyvirus.

Alternatively, next to the expression in host cells such as plant cells the protein or polypeptide of interest can be produced in cell-free translation systems using RNAs derived from the nucleic acid constructs of the present invention.

In the method according to the invention the nucleic acid construct can further optionally comprise interest in large amounts. Vectors that can be used in this other regulatory elements known in the art that are suitable in said method. These include, but are not limited to, elements present in the 5' UTR, 3' UTR and coding nucleotide sequences of homologous and/or heterologous nucleotide sequences, including the Iron Responsive Element (IRE), Translational cis-Regulatory Element (TLRE) or uORFs in 5' UTRs and poly(U) stretches in 3' UTRs. Preferably, said regulatory elements are operably linked to the nucleotide sequences and promotors according to the invention.

When a transformed tissue or cell (e.g., pieces of leaf, stem segments, roots, but also protoplasts or plant cells cultivated by suspension) is obtained with the method according to the invention, whole plants can be regenerated from said transformed tissue or cell in a suitable medium, which optionally may contain antibiotics or biocides known in the art for the selection of transformed cells.

Resulting transformed plants are preferably identified by means of selection. The nucleic acid construct according to the invention therefore preferably also comprises a marker gene which can provide selection or screening capability in a treated plant. Selectable markers are generally preferred for plant transformation events, but are not available for all plant species. Suitable selectable markers can be antibiotic or herbicide resistant genes which, when inserted in some cells of a plant in culture, would confer on those cells the ability to withstand exposure to an antibiotic or a herbicide. Another type of marker gene is one that can be screened by histochemical or biochemical assay, even though the gene cannot be selected for. A suitable marker gene found useful in such plant transformation experience is the GUS gene. Jefferson et al., EMBO J., 6: 3901-3907 (1987), disclose the general protocol for a GUS assay. The GUS gene encodes an enzyme that catalyzes the cleavage of 5-bromo-4-chloro-3-indolyl glucuronide, a substrate that has a blue color upon cleavage. Thus, the use of a GUS gene provides a convenient assay for the detection of the expression of introduced DNA in plants by histochemical analysis of the plants. In an example of a transformation process, the gene sought to be expressed in the plant could be coupled in tandem with the GUS gene. The tandem construct could be transformed into plants, and the resulting plants could be analyzed for expression of the GUS enzyme. Another example of a marker gene is luciferase. An advantage of this marker is the non-destructive procedure of application of the substrate and the subsequent detection. The transformed plants can also be identified by expression of the gene of interest.

In a next step the transformed plant, part or cell thereof is subjected to conditions leading to expression of the protein or polypeptide of interest, and optionally recovering said protein or polypeptide. Recovering steps depend on the expressed protein or polypeptide and the host cell used but can comprise isolation of the protein or polypeptide. When applied to a protein/polypeptide, the term "isolation" indicates that the protein is found in a condition other than its native environment. In a preferred form, the isolated protein is substantially free of other proteins, particularly other homologous proteins. It is preferred to provide the protein in a greater than 40% pure form, more preferably greater than 60% pure form. Even more preferably it is preferred to provide the protein in a highly purified form, i.e., greater than 80% pure, more preferably greater than 95% pure, and even more preferably greater than 99% pure, as determined by SDS-PAGE. If desired, the second nucleotide sequence may be ligated to a heterologous nucleotide sequence to encode a fusion protein to facilitate protein purification and protein detection on for instance Western blot and in an ELISA.

Suitable heterologous sequences include, but are not limited to, the nucleotide sequences encoding for proteins such as for instance glutathione-S-transferase, maltose binding protein, metal-binding polyhistidine, green fluorescent protein, luciferase and beta-galactosidase. The protein may also be coupled to non-peptide carriers, tags or labels that facilitate tracing of the protein, both in vivo and in vitro, and allow for the identification and quantification of binding of the protein to substrates. Such labels, tags or carriers are well-known in the art and include, but are not limited to, biotin, radioactive labels and fluorescent labels.

In a particularly preferred embodiment of the method according to the invention the plant that is used for the expression of the protein or polypeptide of interest is a doubled haploid (homozygous) transgenic *Nicotiana tabacum* plant silenced for Ntp303. The transgenic plant originates from *Nicotiana tabacum* cv. Petit havana which was transformed with antisense ntp303 and selected for via anther culture. Forty independent transformed plantlets were generated from anthers by anther culture in vitro. Four of them were doubled haploids and could produce haploid pollen. The morphological and agronomic characters of these doubled haploids with 1 n gametes were compared with those of their wild type parent. The transgenic plant and the flowers it produces are exactly the same as the wild type. Moreover, it gives a normal amount of pollen, but crossings give no offspring (i.e. the plant is male sterile). However, the pollen can be germinated in vitro and its pollen tube growth is similar to that of wild type pollen. In planta germination of the pollen is poor and the few pollen tubes that are formed stop growing after 10 mm of growth into the style.

Preferably, the protein or polypeptide of interest is expressed in pollen tubes or seed of a plant used in the method according to the invention. Mass culture of pollen tubes in vitro can be established in a germination chamber according to the specifications of Schrauwen and Linskens (1967) Acta Bot. Neerl. 16 (5), 177-179.

Furthermore, a part of the invention is a doubled haploid homozygous transgenic *Nicotiana tabacum* plant silenced for Ntp303. Preferably, said transgenic plant comprises any one of the nucleic acid construct described above. Propagation, harvest and tissue material of said transgenic plant, including, but not limited to, leafs, roots, shoots and flowers, are also a part of the invention.

Yet a further aspect of the invention pertains to ligands that specifically bind to a first nucleotide sequence according to the invention comprised in a RNA molecule, thereby regulating the translation of a second nucleotide sequence encoding a protein or polypeptide of interest operably linked to the first nucleotide sequence.

In one embodiment of the invention the ligand of the invention specifically binds to a first nucleotide sequence comprised in a RNA molecule, whereby the first nucleotide sequence has at least 34% nucleotide sequence identity to the nucleotide sequence of SEQ ID No. 1. The nucleotide sequence represented by SEQ ID No. 1 is in the DNA form, but the skilled worker understands that when this nucleotide sequence is in the RNA form thymine (T) has to be replaced by uracil (U). Preferably, the ligand of the invention specifically binds to a first nucleotide sequence comprised in a RNA molecule, whereby the first nucleotide sequence has at least 36%, more preferably at least 40%, 45%, 50%, 55%, 60%, 65%, 70%, 75%, 80%, 85%, 90%, 95% or 98% nucleotide sequence identity to the nucleotide sequence of SEQ ID No. 1. In a particularly preferred embodiment of the invention the ligand of the invention specifically binds to a first nucleotide sequence comprised in a RNA molecule, whereby the first nucleotide sequence has 100% nucleotide sequence identity to the nucleotide sequence of SEQ ID No. 1. The nucleotide sequence presented herein as SEQ ID No. 1 is as mentioned above the 5' UTR sequence of the ntp303 gene of *Nicotiana tabacum*.

In a further embodiment of the invention the ligand specifically binds to a first nucleotide sequence comprised in a RNA molecule, whereby the first nucleotide sequence comprises a nucleotide sequence that has at least 46% nucleotide sequence identity to nucleotides 104-151 of the nucleotide sequence of SEQ ID No. 1. Preferably, the ligand specifically binds to a first nucleotide sequence comprised in a RNA molecule, whereby the first nucleotide sequence comprises a nucleotide sequence that has at least 48%, 50%, 55%, 60%, 65%, 70%, 75%, 80%, 85%, 90%, 95%, 98% and particularly 100% nucleotide sequence identity to nucleotides 104-151 of the nucleotide sequence of SEQ ID No. 1. In a preferred embodiment of the invention the ligand specifically binds to a first nucleotide sequence (or a part thereof) comprised in a RNA molecule, whereby the first nucleotide sequence is transcribed from the nucleotide sequence that has at least 46% nucleotide sequence identity to nucleotides 104-151 of the nucleotide sequence of SEQ ID No. 1.

In another embodiment of the invention the ligand specifically binds to a first nucleotide sequence comprised in a RNA molecule, whereby the first nucleotide sequence comprises a nucleotide sequence that has at least 51% nucleotide sequence identity to nucleotides 4-76 of the nucleotide sequence of SEQ ID No. 1. Preferably, the ligand specifically binds to a first nucleotide sequence comprised in a RNA molecule, whereby the first nucleotide sequence comprises a nucleotide sequence that has at least 55%, more preferably at least 60%, 65%, 70%, 75%, 80%, 85%, 90%, 95%, 98% and particularly 100% nucleotide sequence identity to nucleotides 4-76 of the nucleotide sequence of SEQ ID No. 1. In a preferred embodiment of the invention the ligand specifically binds to a first nucleotide sequence (or a part thereof) comprised in a RNA molecule, whereby the first nucleotide sequence is transcribed from the nucleotide sequence that has at least 51% nucleotide sequence identity to nucleotides 4-76 of the nucleotide sequence of SEQ ID No. 1.

In yet another embodiment of the invention the ligand according to the invention specifically binds to a first nucleotide sequence comprised in a RNA molecule, whereby the first nucleotide sequence comprises a nucleotide sequence having the nucleotide sequence of nucleotides 27-50 of the nucleotide sequence of SEQ ID No. 1.

In a preferred embodiment of the invention the ligand specifically binds to a first nucleotide sequence (or a part thereof) comprised in a RNA molecule, whereby the first nucleotide sequence is transcribed from the nucleotide sequence having the nucleotide sequence of nucleotides 27-50 of the nucleotide sequence of SEQ ID No. 1.

In a preferred embodiment of the invention the ligand specifically binds to a first nucleotide sequence (or a part thereof) comprised in an at least partly double stranded RNA molecule, whereby the first nucleotide sequence is transcribed from the nucleotide sequence having the nucleotide sequence of nucleotides 14-21 and the complementary strand having the nucleotide sequence of nucleotides 59-66 of the nucleotide sequence of SEQ ID No. 1.

If desired, a combination of the ligands mentioned above can be used.

Ligands according to the invention can be metals, peptides, proteins, lipids, polysaccharides, small organic molecules, nucleotides (including non-naturally occurring ones) and combinations thereof. Preferably, the ligands according to the invention are peptides, proteins, nucleotides or combinations thereof.

Metals that can be used as ligands according to the invention include, but are not limited to, $Mg^{2+}$, $K^+$ (G-quartet), $Fe^{2+}$, $Cu^{2+}$ and $PtCl_2$.

Lipids that can be used as ligands according to the invention include, but are not limited to, lipochitooligosaccharides (LCOs), cationic lipids, anionic lipids and zitterionic lipids.

Polysaccharides that can be used as ligands according to the invention include, but are not limited to, lipochitooligosaccharides (LCDs).

Small organic molecules that can be used as ligands according to the invention include, but are not limited to, caffeine, pophyrine, peptides, haem, aromatic structures and OH (hydroxyl) in combination with $NH_2$ groupes in f.e. neomycine. Preferably, these small organic molecules have a molecular weight of more than 50 yet less than about 2,500 daltons, and most preferably less than about 400 daltons.

Nucleotides that can be used as ligands according to the invention include but are not limited to antisense nucleic acid molecules. The antisense nucleic acid molecules can be selected from antisense RNA molecules, antisense DNA molecules and derivatives thereof, e.g. HNA, fosforothioate-DNA, antisense PNA molecules with lengths of 8-20 units.

Peptides with lengths up to 60 AA (amino acids) that can be used as ligands according to the invention.

An important group of ligands that can be used according to the invention encompasses proteins that are able to interact with RNA. These RNA binding proteins (RBP) appear to mediate inter alia the processing of pre-mRNAs, the transport of mRNA from the nucleus to the cytoplasm, mRNA stabilization, the translational efficiency of mRNA, and the sequestration of some mRNAs. RNA binding proteins that can be used as ligands according to the invention include but are not limited to proteins comprising a RNA binding protein motifs such as inter alia the heterogenous nuclear) ribonucleoprotein (RNP) motif, Arg-rich motif, RGG box, KH motif and double-stranded RNA-binding motif (for review see Burd and Dreyfuss, Science 265:615-621 (1994). These motifs recognize both sequence and structure dependent RNA elements. Furthermore, proteins such as inter alia RNA hairpin-binding factors, proteins with a RNA recognition motif, GAA-binding proteins, RNA-binding proteins with a serine-rich domain, heat shock proteins and cellular nucleic acid binding proteins can be used as ligands.

Preferably, the ligand according to the invention is naturally occurring in the host cell, wherein the first nucleotide sequence comprised in a RNA molecule is present. Alternatively, the ligand can also be introduced into the host cell by methods known in the art.

Use of a ligand according to the invention for regulating translation of a second nucleotide sequence encoding a protein or polypeptide of interest, the second nucleotide sequence operably linked to the first nucleotide sequence is also a part of the present invention. The second nucleotide sequence can encode a homologous or heterologous protein or polypeptide according to the invention. The specific binding of the ligand to the first nucleotide comprised in a RNA molecule can on the one hand lead to a decrease of translation of the second nucleotide sequence encoding the protein or polypeptide of interest. Alternatively, the binding can also lead to an increase of translation. An increase in translation is mediated by the binding of inter alia a protein or polypeptide that specifically binds to a double stranded piece of RNA in the H-I structure (see page 32 lines 2-4). This protein contains an amino acid sequence Ser (Arg/Lys) (Arg/Lys) Xaa (Ala/Pro) Arg Lys (Asn/Gln/His) Lys (SEQ ID NO: 14) in which Xaa is any amino acid and the amino acids in parentheses represent one of two or three alternative amino acids that are considered to be conservative amino acid substitutions.

EXAMPLES

Materials and Methods

Plant Material

Greenhouse-grown plants of *Nicotiana tabacum* L. cv. Petit Havana SR1 were used as the source of pollen and leaf tissue for microprojectile bombardment. To assess the transient expression of the different chimeric genes during pollen development, immature pollen at the late-bicellular stage were aseptically isolated from flower buds of 35 mm length in M1 medium as previously described (Tup et al., (1991) Sex. Plant Reprod. 4(4): 284-287). Transient expression of different gene fusion constructs during pollen tube growth was measured using mature pollen which were isolated from dehiscent tobacco flowers (Herpen et al., (1992) Sex. Plant Reprod. 5, 304-309).

After isolation, the pollen pellet was suspended in 100 μl M1-medium at a density of $10^8$ cells/ml. To fixate the pollen for particle bombardment, the pollen suspension was pipetted onto the surface of a sterile Hybond-N membrane (Amersham) that was placed on 1% agar solidified M1 medium. Following bombardment, the membrane containing late-bicellular or mature pollen was soaked in 10 ml of M1 medium or Read-medium (Read et al., (1993) Protoplasma 174, 101-115.), respectively. The late-bicellular pollen was incubated at 25° C. in the dark at vigorous shaking. After centrifugation, the mature pollen was suspended in a 10-ml tube containing 0.5 ml Read medium followed by a 20 hours incubation in the dark. Treatment of leaf tissue before and after bombardment was performed as described by Hamilton et al., (1992) Plant Mol. Biol. 18, 211-218.

In all cases, bombardments were done within 60 min of placing plant materials onto the solidified medium.

Preparation of Gene Fusion Constructs Containing Different UTRs

In all constructs, either a modified version of the firefly luciferase coding region, luc$^+$, or luciferase cDNA from *Renilla reniformis* (rluc) was used as the reporter gene. The luc$^+$ cDNA was amplified by the polymerase chain reaction (PCR) on the pGL3 vector (Promega) using a forward sequence-specific primer which introduced a NcoI site at the 5' end (5'-ATATCCATGGAAGACGCC; NcoI site underlined; SEQ ID No. 2) and a reverse sequence-specific primer which introduced a BamHI site at the 3' end (5'-ATAT GGATCCTTACACGGCGATC; BamHI site underlined; SEQ ID No. 3). The rluc cDNA was amplified by PCR on the pRL-SV 40 vector (Promega) using the following sequence-specific primers: 5'-GTGT CCATGGATGACTTCGAAAG (NcoI site underlined; SEQ ID No. 4) and 5'-GTGT GGATCCTTATTGTTCATTTTTGAG (BamHI site underlined; SEQ ID No.5). For construction of $^{35S}$syn44 5'/35S 3', the PCR product of luc$^+$ was digested with NcoI and BamHI and, after removal of the luciferase gene, ligated into the NcoI and BamHI sites in pRTS2LUC (Bate et al., (1996) Plant J., 10(4), 613-623). pRTS2LUC (kindly provided by Dr. David Twell) contained the CaMV35S promoter (Topfer et al., 1987), a 44 basepairs long synthetic polylinker (designated as syn44 5' in this article), the luciferase cDNA (Ow et al., 1986) and the CaMV 35S 3' untranslated region (Topfer et al., (1987) Nucl. Acids. Res. 15, 5890).

An almost identical construct was built, $^{35S\ R}$syn44 5'/35S 3', in which the luc$^+$ gene was replaced by the rluc coding region. To obtain a gene fusion construct containing both ntp303 UTRs and the CaMV35S promoter (pRH1-1 $^{35S}$303 5'/303 3'), the syn44 5' UTR was removed from pRH4-1 using XhoI and NcoI restriction enzymes. The ntp303 5' UTR was amplified by PCR on the ntp303 genomic clone (Weterings et al., (1995) Sex. Plant Reprod. 8(1) 11-17) using the following primers with restriction sites incorporated into the 5' end: 5'-GTGT CTCGAGCAAGCTCTAGCAGGAAG (XhoI site underlined; SEQ ID No.6) and 5'-GTGT CCATGGGACGTTGTTTTTTTATTC (NcoI site underlined; SEQ ID No. 7). Following the PCR, the ntp303 5' UTR was obtained with XhoI-NcoI digestion and ligated in the $^{35S}$syn44 5'/35S 3' construct lacking the syn44 5' UTR to create the plasmid $^{35S}$303 5'/35S 3'. The oligonucleotides 5'-ATAT GGATCCATTCTGTAATGATCAATCTG (BamHI site underlined; SEQ ID No. 8) and 5'-ATAT GAGCTCATTTAATGTTTTGTCCTA (SacI site underlined; SEQ ID No. 9) were used to generate the ntp303 3' UTR using the ntp303 genomic clone as template. This PCR fragment was digested with BamHI and SacI and cloned into $^{35S}$303 5'/35S 3' to replace the CaMV 35S 3' UTR and to create $^{35S}$303 5'/303 3'.

Gene fusion constructs containing the ntp303 promoter were made as follow. Using the genomic clone of ntp303 as template, a 578 basepairs long promoter fragment, including the transcription initiation site, was amplified (Weterings et al., 1995) using the primers 5'-ATATAAGCTTGATA-CACTCGCAACGTGTGT (HindIII site underlined; SEQ ID No. 10) and 5'-ATAT CTCGAGGAGCTTGCACTATTCACCAT (XhoI site underlined; SEQ ID No. 11). The amplified ntp303 promoter fragment, that included the region which has been demonstrated to reflects the minimal upstream region of the ntp303 gene that is capable to direct pollen expression, was digested with HindIII and XhoI and, after removal of the CaMV 35S promoter, ligated into $^{35S\ R}$syn44 5'/35S 3', $^{35S}$303 5'/35S 3' and $^{35S}$303 5'/303 3' to create $^R$syn44 5'/35S 3', 303 5'/35S 3' and 303 5'/303 3', respectively. To obtain a construct containing the ntp303 promoter, the ntp303 UTRs and the *Renilla* luciferase cDNA ($^R$303 5'/303 3'), the luc$^+$ gene was digested from 303 5'/303 3' using NcoI and BamHI, after which the rluc coding region was ligated into the NcoI and BamHI sites. The constructs which were regulated by the ntp303 promoter and which expressed the luc$^+$ gene contained a longer version of the synthetic linker than which was used in all the other constructs. This 99-basepairs long synthetic leader was obtained by PCR using the pNBL52-44 plasmid as the template (a kindly gift from Dr. David Twell). This fragment, designated as syn99 5' in this article, was amplified using the following primers: 5'-GTGT CTCGAGTTGCAATTGGATCC (XhoI site underlined; SEQ ID No. 12) and 5'-GTGT CCATGGCCGCGGG (NcoI site underlined; SEQ ID No. 13). After removal of the ntp303 5' UTR from 303 5'/35S 3' and 303 5'/303 3', the syn99 5' UTR was cloned into the XhoI and NcoI sites creating the syn99 5'/35S 3' and syn99 5'/303 3' constructs, respectively.

Constructs containing modifications of the ntp303 5' UTR (A 5' UTR) were all obtained by PCR using the ntp303 5' UTR in the 303 5'/35S 3' construct as starting-material. Fragments which were obtained by PCR were sequenced completely to exclude mismatches within the sequences. All constructs used for transient expression were in the pUC19 plasmid.

Microprojectile Bombardment

Microcarriers, rupture disks and macrocarriers were obtained from Bio-Rad. Preparation and coating of the microcarriers was performed according the manufacture's manual (Bio-Rad). For biolistic transformation of late bicellular pollen and mature pollen, we used per bombardment 250 μg gold particles with a size of 1 μm and 1.6 μm, respectively. The microcarriers were coated with a total amount of 1 μg DNA containing 0.7 μg test plasmid DNA and 0.3 μg normalisation plasmid DNA. Test plasmids containing the ntp303 promoter and the luc$^+$ gene, the CaMV 35S promoter and the luc$^+$ gene, or the ntp303 promoter and the rluc gene were Co-precipitated with the normalisation plasmids $^R$syn44 5'/35S 3', $^{35S}$ $^R$syn44 5'/35S 3' and syn44 5'/35S 3', respectively. syn44 5'/35S 3' is identical to syn99 5'/35S 3', with the exception of containing the SYN44 5' leader instead of the SYN99 5' leader. Microprojectile bombardment was performed using the helium-driven PDS-1000/He System of Bio-Rad. For biolistic transformation of pollen and leaves, the following bombardment parameters were used: a target distance of 6 cm, a gap distance of ¼ inch, a microprojectile/stopping screen distance of 8 mm, a chamber vacuum of 28 mm Hg, and a burst pressure of the rupture disks of 1100 psi.

Luciferase Assays

After particle bombardment and incubation of the tissues, quantitative determination of transient expression of the different gene fusion constructs was performed using the commercial available Dual-Luciferase™ Reporter Assay System (Promega). In this assay, the activities of the LUC+ and RLUC luciferases were measured sequentially from a single sample extract using a luminometer provided with two auto-injectors (Wallac 1420 VICTOR$^2$™, EG&G Wallac). Preparation of the buffers used in the assay was performed according the manufacture's manual (Promega). After incubation, the developing pollen were transferred into a 10-ml Greiner tube and collected by centrifugation for 2 minutes at 2,500 rpm. Germinating pollen were collected by centrifugation for 5 minutes at 1,000 rpm. In all cases, the pollen pellet was resuspended in 100 μl 1× passive lysis buffer (Promega) and grinded in liquid nitrogen. The pollen extracts were stored at −70° C. until use for the luciferase activity assay. Extracts (10 μl) were pipetted in a microtiter plate after which the plate was placed in the luminometer. 100 μl of Luciferase Assay Reagent II (Promega) was automatically injected followed, after 2 seconds, by a counting of the photons for 10 seconds. Immediately after the quantification of the LUC$^+$ luminescence, the reaction was quenched, and the RLUC reaction was initiated after automatically addition of 100 μl of Stop&Glo™ Reagent (Promega). RLUC luminescence was also measured for 10 seconds, 2 seconds after injection. To compensate for variability of the expression of a same test reporter gene between independent experiments, the ratio of LUC$^+$: RLUC was determined. For each construct, at least six independent bombardment were performed.

Example 1

UTR Gene Fusion Constructs

Several gene fusion constructs containing the ntp303 promoter, the firefly luciferase reporter gene and different combinations of 5'- and 3' UTRs were built to investigate the ability of the UTRs of ntp303 to modulate gene expression during pollen development and pollen tube growth (FIG. 1). The names of the constructs refer to their 5' UTR and 3' UTRs (5' UTR/3' UTR). The abbreviation '35S' or 'R' which is given in uppercase before a construct name indicates that the construct contains the CaMV 35S promoter or *Renilla* luciferase coding region, respectively.

The UTR gene fusion constructs were introduced by particle bombardment into developing or mature pollen. Their transient expression was measured after a period of 20 hours ill vitro development or germination by luminescence measurements. To correct for differences in bombardment efficiencies, a second construct was co-bombarded containing the ntp303 promoter, a synthetic 5' UTR (syn44 5'), the cauliflower mosaic virus termination sequence (35S 3') and a luciferase reporter gene from *Renilla* ($^R$syn44 5'/35S 3'). The transient expression value of the firefly luciferase construct was normalized to the value of the *Renilla* luciferase construct.

Figure 2:
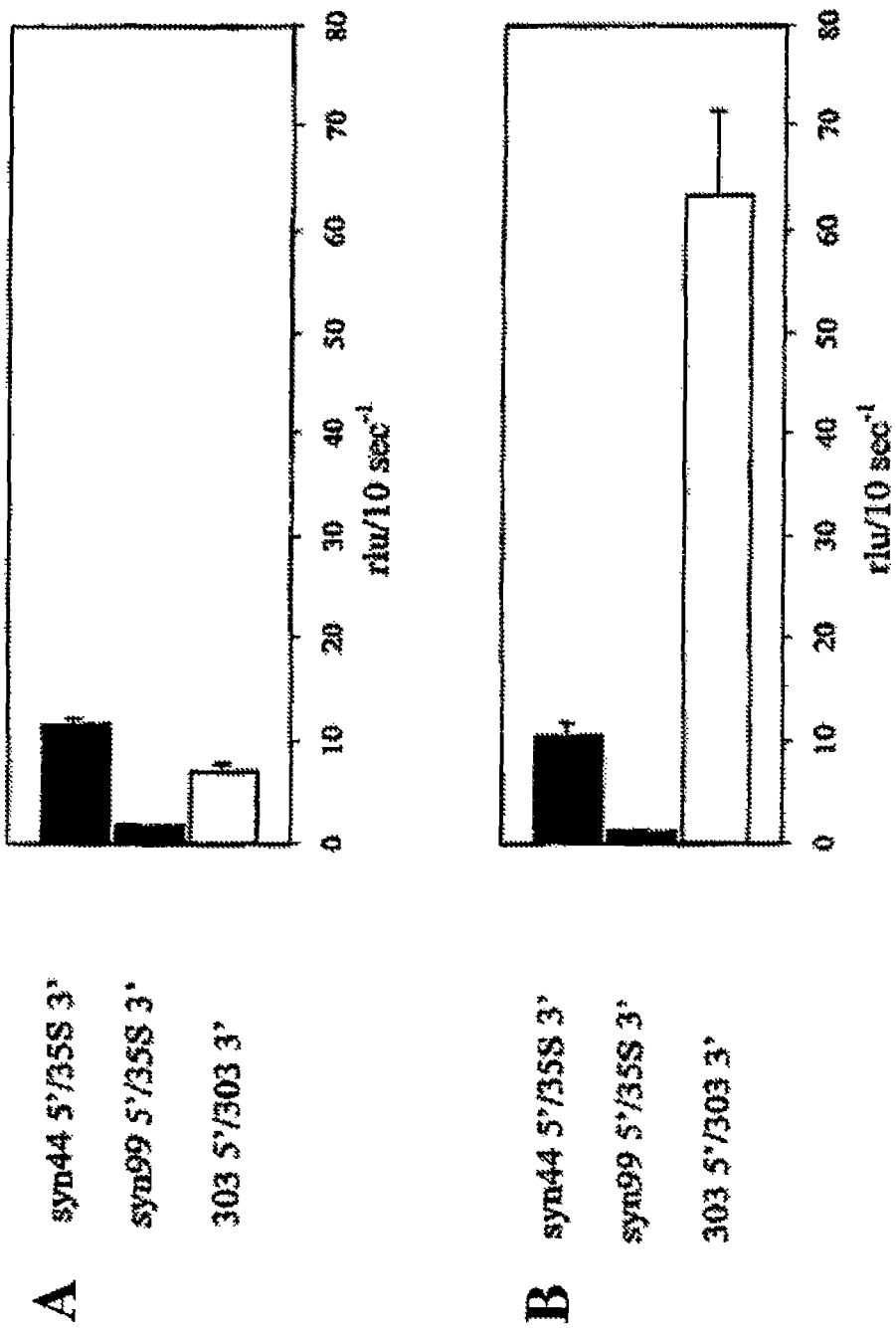
FIG. 2: Transient expression of UTR gene fusion constructs in developing pollen (A) and growing pollen tubes (13). Rlu/10 sec$^{-1}$ means the relative light units per 10 seconds measuring time as determined by normalization of the absolute expression of the test construct with that of the reference construct.

The effect of ntp303 UTRs on transient expression during pollen development and pollen tube growth was investigated by comparing the expression level of a construct containing the ntp303 UTRs (303 5'/303 3') with that of constructs containing control UTRs (the syn99 5' or syn44 5' UTR and the 35S 3' UTR). After 20 hours of pollen tube growth, the expression of 303 5'/303 3' was approximately 60- and 6-fold higher than that of syn99 5'/35S 3' and syn44 5'/35S 3', respectively (FIG. 2b). The differences in the expression level were already observed in tubes of pollen which were bombarded 5 hours before. Such large differences in expression level were not observed in developing pollen incubated for 20 hours after bombardment of the ntp303 UTRs construct. Here, the ntp303 UTRs gave rise to an expression level that was approximately 4-fold higher than that of syn99 5'/35S 3' UTRs and slightly lower than that of syn44 5'/35S 3' (FIG. 2a). The expression levels of the constructs containing the control UTRs were more or less the same during pollen development and pollen tube growth (FIGS. 2a and 2b). This clearly illustrates that expression mediated by these control UTRs is independent of the developmental stage in which they were tested.

Figure 3:
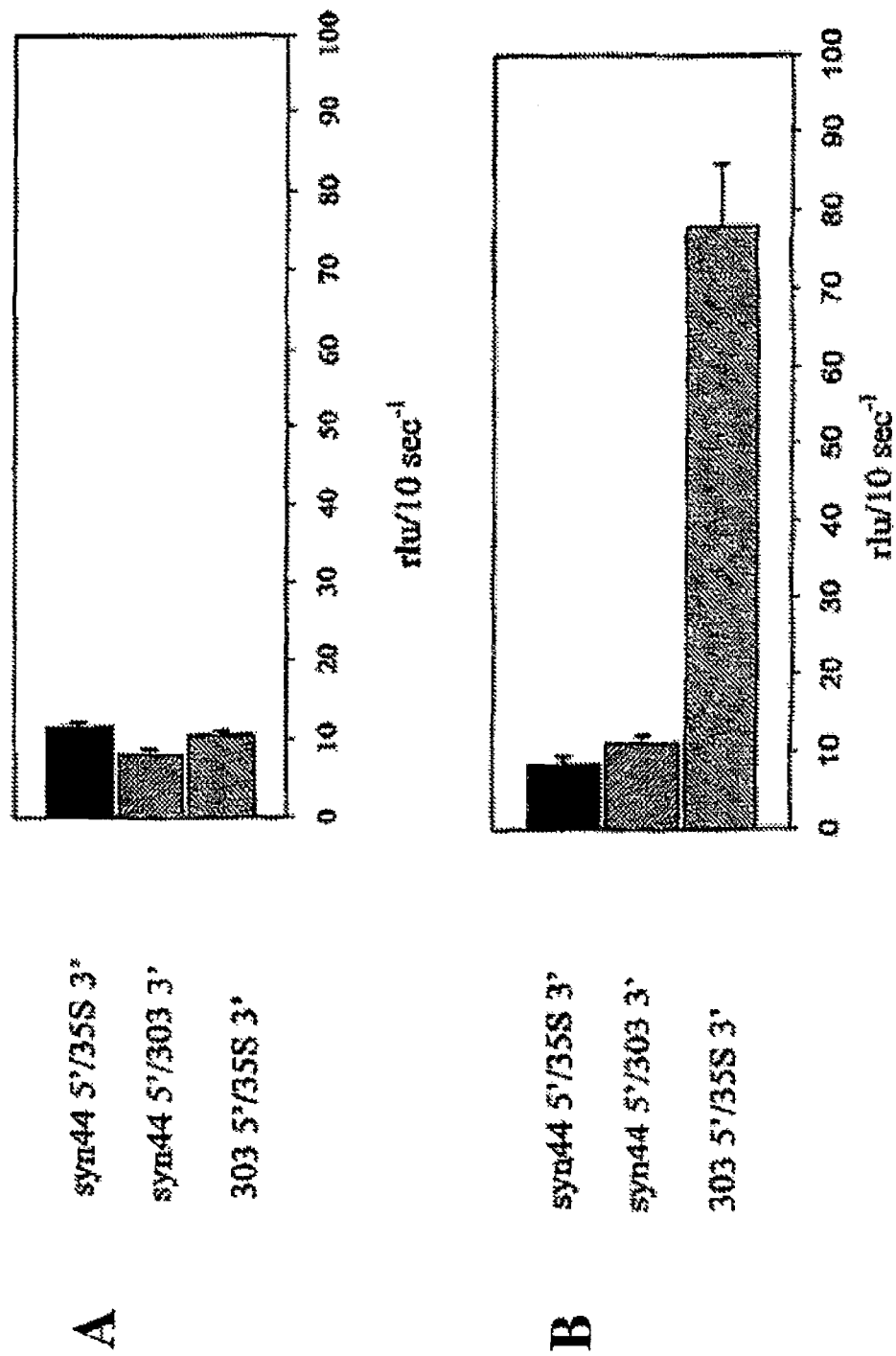
FIG. 3: Transient expression of UTR gene fusion constructs in developing pollen (A) and growing pollen tubes (B). Rlu/10 sec$^{-1}$ means the relative light units per 10 seconds measuring time as determined by normalization of the absolute expression of the test construct with that of the reference construct.

To examine whether the 5' UTR or the 3' UTR of the ntp303 mRNA determines the level of gene expression during pollen development and pollen tube growth, transient expression levels of gene fusion constructs containing the ntp303 5'/35S 3' or the syn44 5'/ntp303 3' UTRs were compared with that of syn44 5'/35S 3'. During pollen tube growth, the ntp303 5' UTR increased the expression of the luciferase gene to a level that was almost 8-fold higher than the control 5' UTR (FIG. 3b). This enhancement effect was absent in the ntp303 3' UTR construct. No significant differences in expression level of the control UTRs and the ntp303 UTR containing constructs were observed during pollen development (FIG. 3a).

Figure 4:
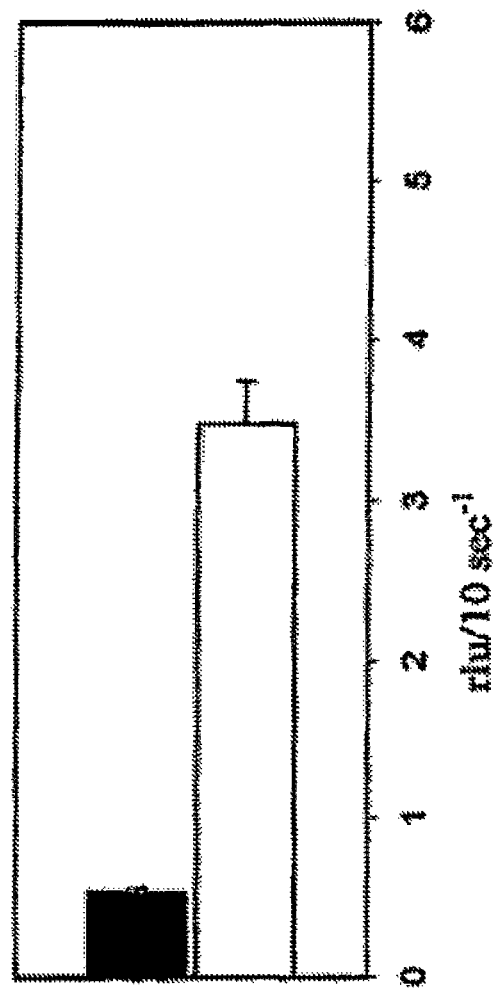
FIG. 4: Transient expression of UTR gene fusion constructs containing the *Renilla* luciferase coding region in growing pollen tubes. Rlu/10 sec$^{-1}$ means the relative light units per 10 seconds measuring time as determined by normalization of the absolute expression of the test construct with that of the reference construct.

To exclude the possibility that the expression enhancement mediated by the ntp303 5' UTR in growing pollen tubes was the result of a specific interaction between the 5' UTR and the firefly luciferase coding region, the firefly luciferase coding region was replaced by the *Renilla* luciferase coding region in the constructs syn44 5'/35S 3' and 303 5'/303 3'. The firefly and the *Renilla* luciferase mRNAs exhibit no significant sequence identity with each other. Normalization of the expression of these constructs was established by co-bombardment with a construct containing the syn44 5' UTR, the 35S termination sequence and the firefly luciferase coding region. As is shown in FIG. 4, the ntp303 UTRs gave rise to an expression level that was approximately 7-fold higher than that of the control UTRs.

Since this enhancement effect of the ntp303 5' UTR was also found for firefly luciferase mRNAs, this excludes a specific interaction between the ntp303 5' UTR and the coding region.

Example 2

Translational Enhancement During Pollen Tube Growth

To investigate whether the enhancement mediated by the ntp303 5' UTR during pollen tube growth was either the result of a post-transcriptional regulation event or of a burst in transcription (i.e. transcriptional regulation), we determined the expression and transcription levels of syn99 5'/35S 3', 303 5'/35S 3' and syn99 5'/303 3' (table 1). 10 µg of total RNA isolated from a pollen extract that was also used for the determination of the expression level as measured from the luciferase activity, was hybridized with a $^{32}$P-labeled luciferase probe. The transcription level was determined by calculation of the ratio of the hybridization signal of the firefly luciferase mRNA to the Renilla luciferase mRNA hybridization signal of the co-bombarded $^R$syn44 5'/35S 3' construct. After 20 hours of pollen tube growth, the ntp303 5' UTR showed a relative transcription level that was approximately 2-fold higher than that of the syn99 5' UTR. The construct containing the ntp303 5' UTR increased the relative expression 50-fold as compared to syn99 5'/35S 3'. Thus, pollen tube growth chimeric luciferase transcripts containing the ntp303 5' UTR are translated more efficiently than luciferase mRNAs containing the control 5' UTR.

TABLE 1

Analysis of the relative transcription (represented as relative luc mRNA abundance) and translation (represented as relative LUC activity) levels of different UTR gene fusion constructs. See results section for a description of the followed methodology. The values in parentheses represents the relative transcription and translation levels after normalization to the relative values of the syn99 5'/35S 3' construct. Measurements were assayed after 20 hours of pollen tube growth.

| Construct | Relative luc mRNA Abundance | Relative LUC Activity (rlu/10 sec$^{-1}$) |
|---|---|---|
| syn99 5'/35S 3' | 1.36 SE ± 0.17 (1.00) | 1.02 SE ± 0.21 (1.00) |
| 303 5'/35S 3' | 3.70 SE ± 0.22 (2.72) | 50.60 SE ± 0.22 (49.61) |
| syn99 5'/35S 3' | 1.81 SE ± 0.22 (1.33) | 2.50 SE ± 0.42 (2.45) |

Example 3

Figure 5:
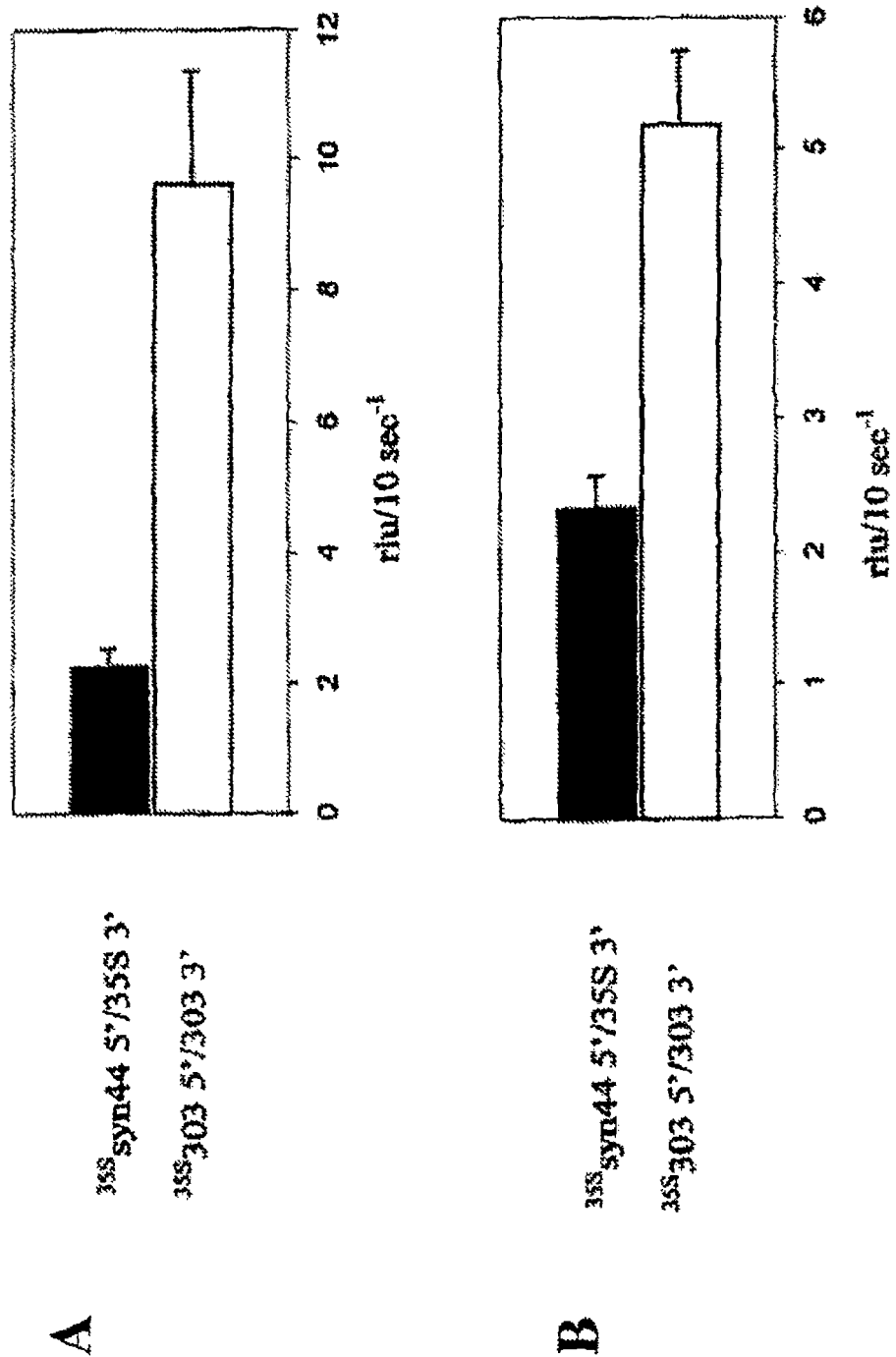
FIG. 5: Transient expression of UTR gene fusion constructs containing the CaMV 35S promoter in growing pollen tubes (A) and young leaves (B3). Rlu/10 sec$^{-1}$ means the relative light units per 10 seconds measuring time as determined by normalization of the absolute expression of the test construct with that of the reference construct.

The 5' UTR-Mediated Enhancement of Gene Expression also Occurs in Other Cells Hopes than Growing Pollen Tubes To test whether the ntp303 5' UTR mediated enhancement of expression in growing pollen tubes was restricted to a pollen-specific environment, the constructs syn44 5'/35S 3' and 303 5'/303 3' were reconstructed by replacing their ntp303 promoter with the CaMV 35S promoter. The CaMV 35S promoter is almost inactive in pollen tubes, but highly active in sporophytic tissues. After particle bombardment of these constructs into mature pollen and young leaves followed by 20 hours of in vitro incubation, transient expression was assayed. Normalization of the expression level of these constructs was done with the expression level of a co-bombarded construct containing the CaMV 35S promoter, the syn44 5' UTR, the Renilla luciferase reporter gene and the 35S 3' UTR. In growing pollen tubes, the ntp303 5' UTR increased the transient expression to a level that was approximately S-fold higher than the control UTRs (FIG. 5a). The differences in the expression level approached that of the constructs containing the same UTR combinations but linked to the ntp303 promoter (compare FIGS. 5a and 2b). In young leaves, the ntp303 5' UTR increased the expression to a level that was approximately 2-fold higher than the control UTRs (FIG. 5b). These data demonstrate that the ntp303 5' UTR-mediated enhancement of expression also occurs in other cell types than growing pollen tubes, such as sporophytic cells. However, the ntp303 5' UTR-mediated enhancement of expression is highest in growing pollen tubes.

Example 4

Figure 6:
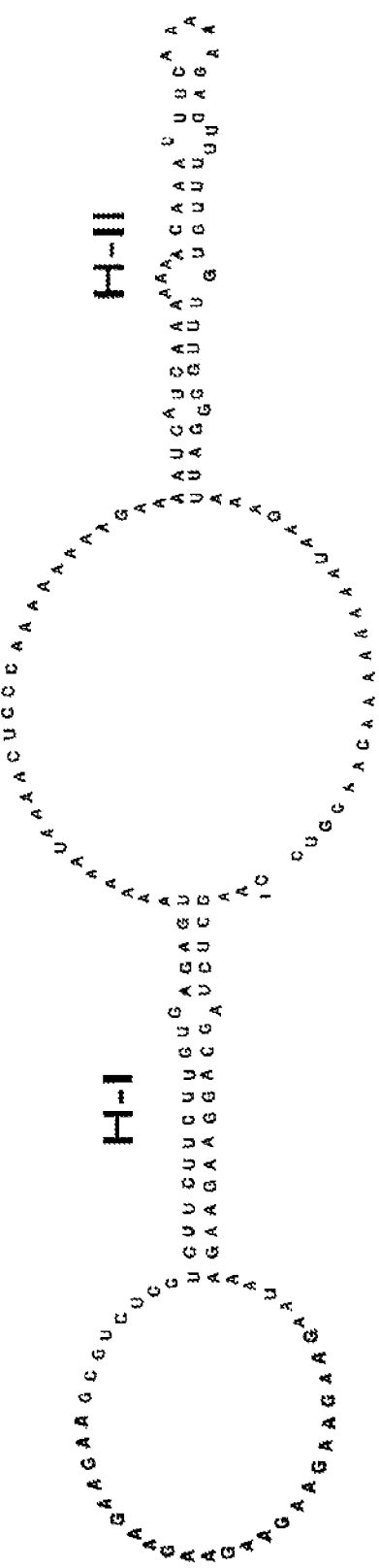
FIG. 6: Predicted secondary structure of the 5' UTR of ntp303. Structure prediction and the calculation of the ΔG value was performed using the RNAdraw software package. H-I (nucleotides 4-76 of SEQ ID NO: 1) and H-II (nucleotides 104-151 of SEQ ID NO: 1) represents two predicted hairpin-loop structures. See result section for a description of the 5' UTR.
Figure 7A:
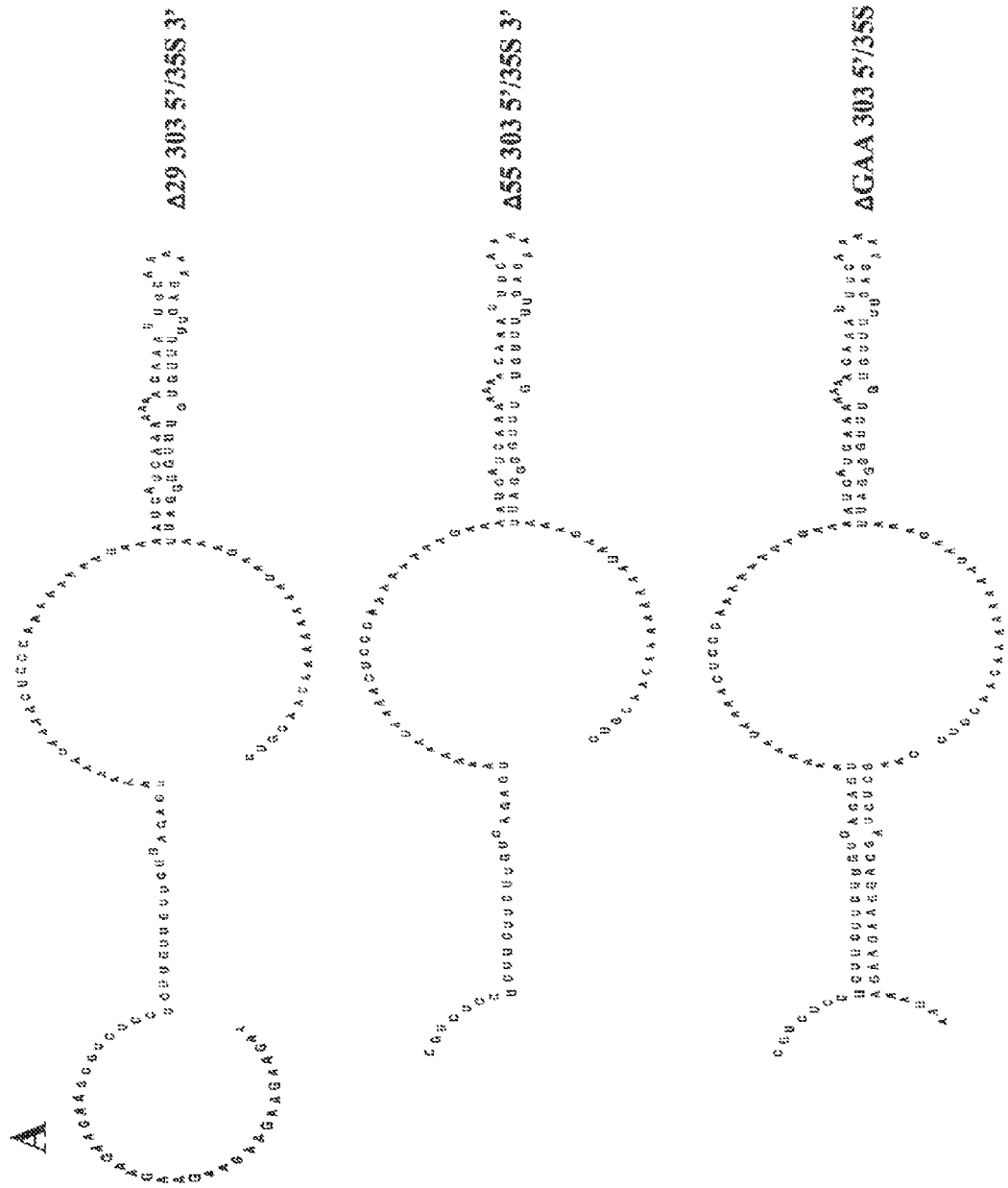
FIG. 7A shows the sequences for Δ29 303 5'/35s 3' (SEQ ID NO: 15); Δ55 303 5'/35S 3'(SEQ ID NO: 16); and ΔGAA 303 5'/35S 3' (SEQ ID NO: 17).
Figure 7B:
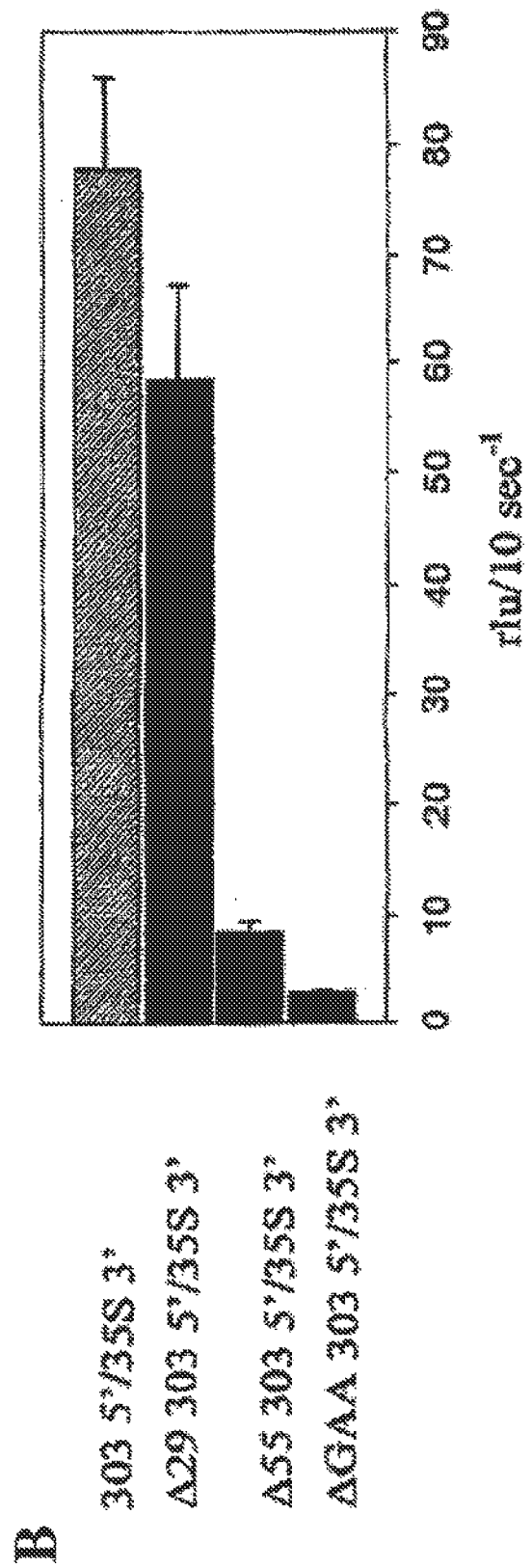
FIG. 7B includes 303 5'/35S 3'(SEQ ID NO: 18).
Figure 7C:
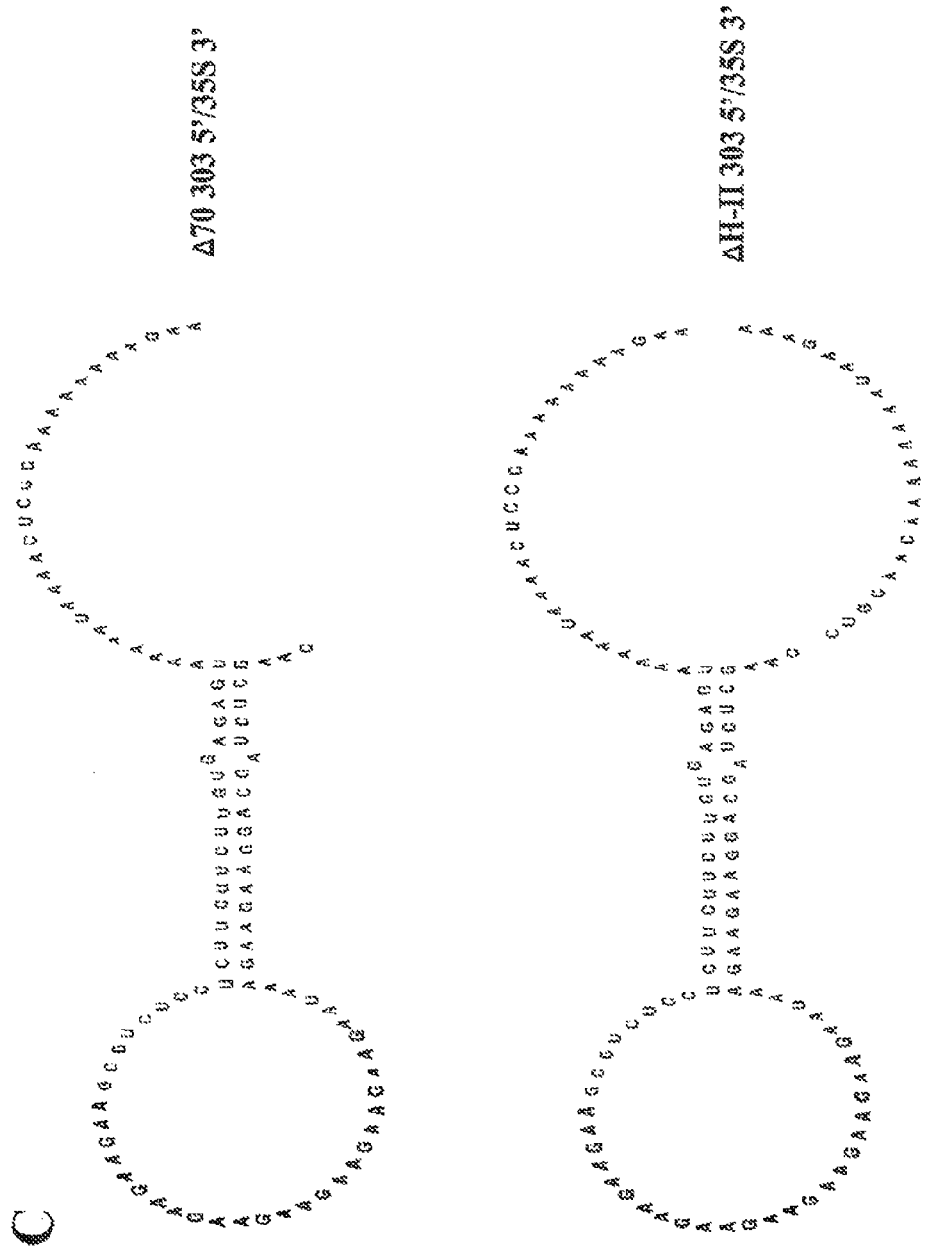
FIG. 7C shows the sequences for Δ70 303 5'/35s 3' (SEQ ID NO: 19) and ΔH-II 303 5'/35S 3' (SEQ ID NO: 20).
Figure 7D:
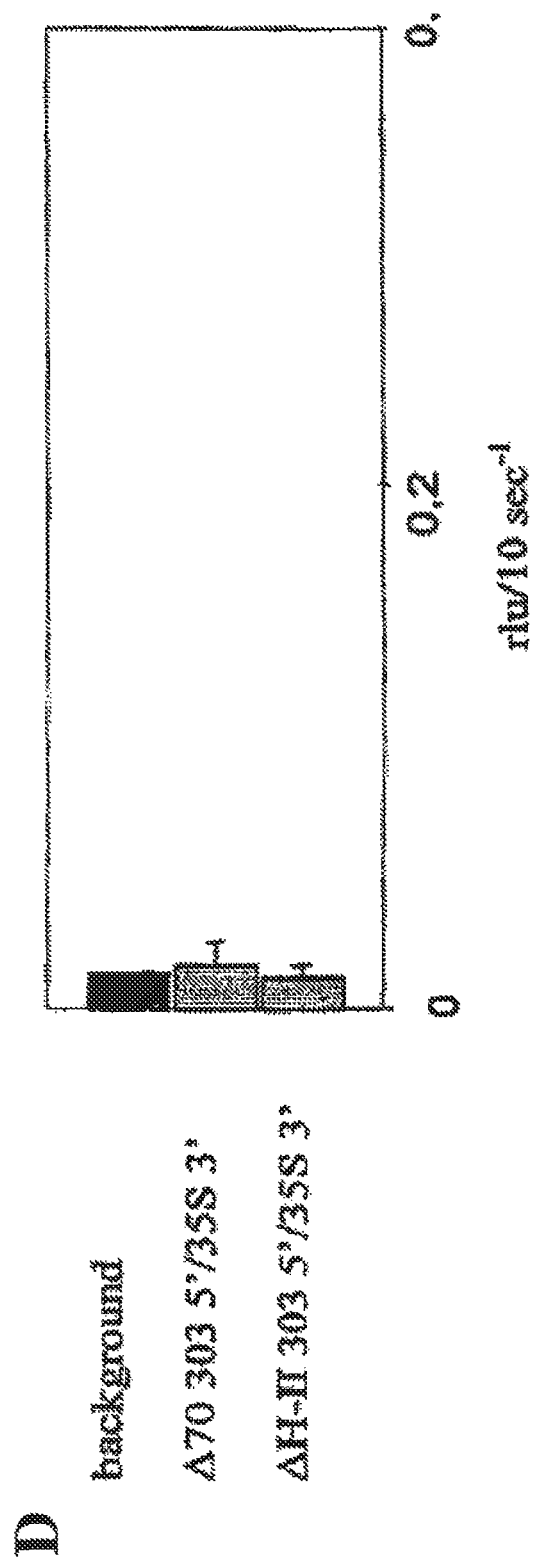

The Enhancement of Expression Dung Pollen Tube Growth is Attributable to Specific Regions within the ntp303 5' UTR FIG. 6 illustrates the predicted secondary structure of the ntp303 5' UTR as analyzed with the RNAdraw software package (Hofacke et al., (1994) Chem. Monthly 125, 167-188). There are two putative stem-loop structures designated H-I (nucleotides 4-76 of SEQ ID No. 1) and H-II (nucleotides 104-151 of SEQ ID No. 1). The H-I stem-loop structure is located at the 5'-terminus and has a calculated energy value (ΔG) of −64 kJ/mol. This structure contains eight repeats of a GAA triplet (nucleotides 27-50 of SEQ ID No. 1) in the external loop and a double stranded RNA in the stem of the predicted H-I structure, consisting of GAAGAAGA (14-21) and the complementary strand TCT-TCTTC (59-66). The H-II structure is located 22 nucleotides upstream from the translation initiation site and has a calculated energy value (ΔG) of −26 kJ/mol. The effect of sequences that reside within the H-I and H-II structures on enhancement of expression during pollen tube growth was investigated by a series of ntp303 5' UTR deletion constructs (FIGS. 7a and c). These constructs were bombarded into mature pollen and their expression was assayed after 20 hours of pollen tube growth (FIGS. 7b and d). An almost complete inactivation of reporter gene expression was achieved after deletion of the last 70 nucleotides at the 3' terminus of the ntp303 5' UTR which included the complete H-II structure (Δ70 303 5'/35S 3' (SEQ ID NO: 19)) (FIG. 7d). The same was true after internal deletion of only the H-II structure (ΔH-II 303 5'/35S 3' (SEQ ID NO: 20)) (FIG. 7d). In both cases, the expression values were in the same range as the background values (i.e. the measured autoluminescence of the luciferine substrate). FIG. 7b shows the transient expression of gene fusion constructs with deletions within the H-I stem-loop structure. The lowest level of transient expression was found after internal deletion of the (GAA)$_8$ repeat (ΔGAA 303 5'/35S 3' (SEQ ID NO: 17)). This expression level was comparable with the expression level of the control construct containing the syn99 leader (data not shown). A decrease in transient expression of approximately 94% occurred after deletion of the first 55 nucleotides (Δ55 303 5'/35S 3' (SEQ ID NO: 16)) at the 5' terminus including the (GAA)$_8$ repeat. Deletion of the first 29 nucleotides at the 5' terminus of the ntp303 5' UTR (Δ29 303 5'/35S 3' (SEQ ID NO: 15)) caused only a slight decrease in transient expression compared to that of the unmodified ntp303 5' UTR. These results clearly demonstrate that luciferase transcripts which contain deletions within the ntp303 5' UTR are expressed to a lower level than transcripts containing the unmodified ntp303 5' UTR. Deletions within or of the H-I or H-II structure caused a different reduction in transient expression. Absence of the enhancement effect was observed after deletion of the (GAA)$_8$ repeat, whereas deletion of the complete H-II structure caused a complete collapse in expression.

Example 5

The H-1 and H-II Structures in the ntp303 5'UTR Influence the Translation Efficiency Efficiency Whether the decrease in transient expression of the 5' UTR deletion constructs was the result of a change in the transcription or translation efficiency, was investigated by measuring the relative transcription and translation levels of some of the ntp303 5' UTR deletion constructs (table 2). The relative transcription levels of the constructs containing deletions of the complete H-II structure (Δ70 303 5'/35S 3' and ΔH-II 303 5'/35S 3') dropped to a level that was lower than that of syn99 5'/35S 3'. Internal deletion of the (GAA)$_8$ repeat (ΔGAA 303 5'/35S 3') resulted in a relative transcription level that was somewhat lower than the transcription level of the construct containing the unmodified ntp303 5' UTR, but the relative transcription levels remained higher than that of the construct containing the synthetic 5' UTR. In contrast to the effects of either the deletion of the (GAA)$_8$ repeat or the H-II structure on the relative transcription level, a more drastic effect was observed for the relative translation levels. A drastic decrease in the relative translation level was observed after deletion of the H-II structure, the values of the normalized translation level were in the range of the background values. Deletion of the (GAA)$_8$ repeat revealed an almost 2-fold lower relative translation level compared to 303 5'/303 3'. From these data, we conclude that the drop in expression observed after deletion of either the H-I- or H-II structures is mainly the result of a decrease in the translation efficiency. The most severe effect on the decrease in the translation efficiency was found after deletion of the H-II structure.

TABLE 2

Analysis of the relative transcription (represented as relative luc mRNA abundance) and translation (represented as relative LUC activity) levels of different ntp303 5' UTR gene fusion constructs. See results section for a description of the followed methodology. The values in parentheses represents the relative transcription and translation 33 levels after normalization to the relative values of the syn99 5'/35S 3' construct. Measurements were assayed after 20 hours of pollen tube growth.

| Construct | Relative luc mRNA Abundance (counts) | Relative LUC Activity (rlu/10 sec$^{-1}$) |
|---|---|---|
| 303 5'/35S 3' | 2.97 SE ± 0.09 (2.18) | 31.08 SE ± 5.61 (30.47) |
| ΔAAG 303 5'/35S 3' | 2.30 SE ± 0.51 (1.69) | 17.49 SE ± 4.76 (17.15) |
| Δ70 303 5'/35S 3' | 1.13 SE ± 0.06 (0.83) | 0.01 SE ± 0.00 (0.01) |
| ΔH-II 303 5'/35S 3' | 0.82 SE ± 0.09 (0.60) | 0.01 SE ± 0.00 (0.01) |

What is claimed is:

1. A nucleic acid construct comprising a first nucleotide sequence that has at least 90% nucleotide sequence identity with the nucleotide sequence of SEQ ID NO: 1, wherein said first nucleotide sequence comprises a nucleotide sequence that has at least 98% nucleotide sequence identity to nucleotides 104-151 of the nucleotide sequence of SEQ ID NO: 1 and wherein said first nucleotide sequence comprises a nucleotide sequence that comprises a repeat of at least 8 GAA units and has at least 98% nucleotide sequence identity to nucleotides 4-76 of the nucleotide sequence of SEQ ID NO: 1, wherein said first nucleotide sequence is operably linked to a second nucleotide sequence encoding a protein wherein said protein is heterologous and wherein said first nucleotide sequence results in an increase in translation of said second nucleotide sequence.

2. The nucleic acid construct of claim 1, wherein the second nucleotide sequence encoding the protein is further operably linked to a promotor.

3. The nucleic acid construct of claim 1, wherein the first nucleotide sequence comprises the sequence of SEQ ID NO: 1.

4. A recombinant animal, mammalian, plant, fungal or bacterial host cell containing one or more copies of the nucleic acid construct as defined by claim 1.

5. A method for expressing a polypeptide of interest in a cell, wherein the cell is a plant, fungal, bacterial, animal or mammalian cell, comprising the steps of:
   a. providing a nucleic acid construct comprising:
      i) a first nucleotide sequence as defined in claim 1, wherein said first nucleotide sequence is operably linked to
      ii) a second nucleotide sequence encoding a polypeptide of interest, and wherein said first nucleotide sequence results in an increase in translation of said second nucleotide sequence, and further operably linked to
      iii) a promoter; and
   b. transforming the cell with said nucleic acid construct to obtain a transformed cell; and
   c. expressing the polypeptide in said transformed cell.

6. The method of claim 5, wherein said first nucleotide sequence comprises the sequence of SEQ ID NO: 1.

7. The method of claim 5, wherein the polypeptide of interest is heterologous to said cell.

8. The method of claim 5, wherein the polypeptide is expressed in a cell of a doubled haploid homozygous transgenic *Nicotiana tabacum* plant silenced for ntp303.

9. The method of claim 5, wherein the polypeptide is expressed in a pollen or seed of a plant that comprises said plant cell.

10. The method of claim 5, wherein the promoter of (a)(iii) is heterologous to said second nucleotide sequence.

11. The method of claim 5, wherein the first nucleotide sequence comprises a sequence forming an HI and HII structure.

12. The method of claim 5, wherein the first nucleotide sequence is DNA.

13. The method of claim 5, wherein the first nucleotide sequence is RNA.

14. The method of claim 5, further comprising step (d) recovering said polypeptide.

15. A recombinant animal, mammalian, plant, fungal or bacterial host cell containing one or more copies of a nucleic acid construct comprising a first nucleotide sequence as defined in claim 1, wherein said first nucleotide sequence is operably linked to a second nucleotide sequence encoding a protein, wherein said first nucleotide sequence results in an increase in translation of said second nucleotide sequence.

16. The nucleic acid construct of claim 2, wherein the first nucleotide sequence is operably linked to the promoter.

17. The nucleic acid construct of claim 1, wherein said first nucleotide sequence comprises a nucleotide sequence that has 100% nucleotide sequence identity to nucleotides 104-151 of the nucleotide sequence of SEQ ID NO: 1.

* * * * *